United States Patent [19]

Hamill et al.

[11] E Patent Number: Re. 32,455

[45] Reissued Date of Patent: Jul. 7, 1987

[54] A-21978 ANTIBIOTICS AND PROCESS FOR THEIR PRODUCTION

[75] Inventors: Robert L. Hamill, Greenwood; Marvin M. Hoehn, Indianapolis, both of Ind.

[73] Assignee: Eli Lilly and Company, Indianapolis, Ind.

[21] Appl. No.: 780,734

[22] Filed: Sep. 26, 1985

Related U.S. Patent Documents

Reissue of:

[64] Patent No.: 4,331,594
Issued: May 25, 1982
Appl. No.: 206,749
Filed: Nov. 14, 1980

U.S. Applications:

[60] Continuation-in-part of Ser. No. 41,274, May 21, 1979, abandoned, which is a division of Ser. No. 951,695, Oct. 16, 1978, Pat. No. 4,208,403.

[51] Int. Cl.[4] ..... C07C 103/52

[52] U.S. Cl. ..... 530/317; 424/115; 435/117; 530/300; 530/318; 530/320

[58] Field of Search ..... 530/318, 320, 317

[56] References Cited

PUBLICATIONS

J. Shoji, et al., "The Total Structure of Cerexin A", *Journal of Antibiotics*, 29 (12) 1268–1274 (1976).

J. Shoji, et al., "The Structure of Cerexin B", Ibid., 29 (12) 1275–1280 (1976).

J. Shoji, et al., "The Structure of Brevistin", Ibid., 29 (4) 380–389 (1976).

*Primary Examiner*—Dale R. Ore

*Attorney, Agent, or Firm*—Nancy J. Harrison; Leroy Whitaker

[57] ABSTRACT

Antibiotic A-21978C complexes, in particular the A-21978C complex, comprising microbiologically active, related factors, $C_0$, $C_1$, $C_2$, $C_3$, $C_4$, and $C_5$. A-21978 complex and A-21978C complex are produced by submerged aerobic fermentation of Streptomyces roseosporus NRRL 11379. The individual A-21978C factors are separated and isolated by chromatography. The A-21978 and A-21978C complexes, the A-21978C factors, and pharmaceutically acceptable salts thereof are antibacterial agents and improve growth promotion in poultry.

18 Claims, 7 Drawing Figures

A-21978 ANTIBIOTICS AND PROCESS FOR THEIR PRODUCTION

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation-in-part of application Ser. No. 41,274, filed May 21, 1979, now abandoned which in turn is a divisional of application Ser. No. 951,695, filed Oct. 16, 1978, which issued as U.S. Pat. No. 4,208,403, on June 17, 1980.

BACKGROUND OF THE INVENTION

1. Field of the Invention

Although there are many known antibacterial agents, the need for improved antibiotics continues. Antibiotics differ in their effectiveness against pathogenic organisms, and organism strains which are resistant to currently used antibiotics continually develop. In addition, individual patients often suffer serious reactions to specific antibiotics, due to hypersensitivity and/or to toxic effects. There is, therefore, a continuing need for new and improved antibiotics.

2. The Prior Art

The A-21978C antibiotics are closely related, acidic peptide antibiotics. Members of this class of antibiotics which were previously known include crystallomycin, amphomycin, zaomycin, aspartocin, and glumamycin [see T. Korzybski, Z. Kowszyk-Gindifer and W. Kurylowicz, "Antibiotics-Origin, Nature and Properties," Vol. I, Pergamon Press, New York, N.Y., 1967, pp. 397–401 and 404–408]; tsushimycin [J. Shoji, et al., J. Antibiotics 21, 439–443 (1968)]; laspartomycin [H. Naganawa, et al., J. Antibiotics 21, 55-(1968)]; brevistin [J. Shoji and T. Kato, J. Antibiotics 29, 380–389 (1976)]; cerexin A [J. Shoji, et al., J. Antibiotics 29, 1268–1274 (1976)] and cerexin B [J. Shoji and T. Kato, J. Antibiotics 29, 1275–1280 (1976)]. Of these antibiotics, brevistin, cerexin A and cerexin B are believed to be the prior art antibiotics which are most closely related to the new A-21978C antibiotics.

SUMMARY OF THE INVENTION

This invention relates to antibiotic substances. In particular, it relates to antibiotic complexes comprising several factors. The A-21978 complex contains major factor C and as yet uncharacterized factors A, B, D and E. A-21978 factor C is a complex of closely related antibiotic factors, including individual A-21978C factors $C_0$, $C_1$, $C_2$, $C_3$, $C_4$, and $C_5$. A-21978 factor C is, therefore, designated herein as A-21978C complex. The salts of the A-21978 and A-21978C complexes and of individual A-21978C factors $C_0$, $C_1$, $C_2$, $C_3$, $C_4$ and $C_5$ are also part of this invention.

The term "complex" as used in the fermentation art and in this specification refers to a mixture of coproduced individual antibiotic factors. As will be recognized by those familar with antibiotic production by fermentation, the number and ratio of individual factors produced in an antibiotic complex will vary, depending upon the fermentation conditions used. In the A-21978C complex factors $C_1$, $C_2$, and $C_3$ are major factors, and factors $C_0$, $C_4$, and $C_5$ are minor factors.

The antibiotic substances of this invention are arbitrarily designated herein as A-21978 antibiotics. In discussions of utility, the term "A-21978 antibiotic" will be used, for the sake of brevity, to denote a member selected from the group consisting of A-21978 complex, A-21978C complex and A-21978C factors $C_0$, $C_1$, $C_2$, $C_3$, $C_4$, and $C_5$, and the pharmaceutically acceptable salts thereof.

The A-21978 complex is produced by culturing Streptomyces roseosporus NRRL 11379 under submerged aerobic fermentation conditions until a substantial level of antibiotic activity is produced. The A-21978 complex is separated by filtering the fermentation broth, lowering the pH of the filtrate to about pH 3, allowing the complex to precipitate, and separating the complex by filtration. The separated complex may be further purified by extraction techniques. For isolation of the individual A-21978C complex and factors, chromatographic separations are required. The A-21978 antibiotics of this invention inhibit the growth of pathogenic organisms, especially gram-positive bacteria.

DESCRIPTION OF THE DRAWINGS

Infrared absorption spectra (KBr pellet) of the following A-21978C antibiotics (as sodium salts) are presented in the accompanying drawings as follows.

DETAILED DESCRIPTION OF THE INVENTION

Figure 1:
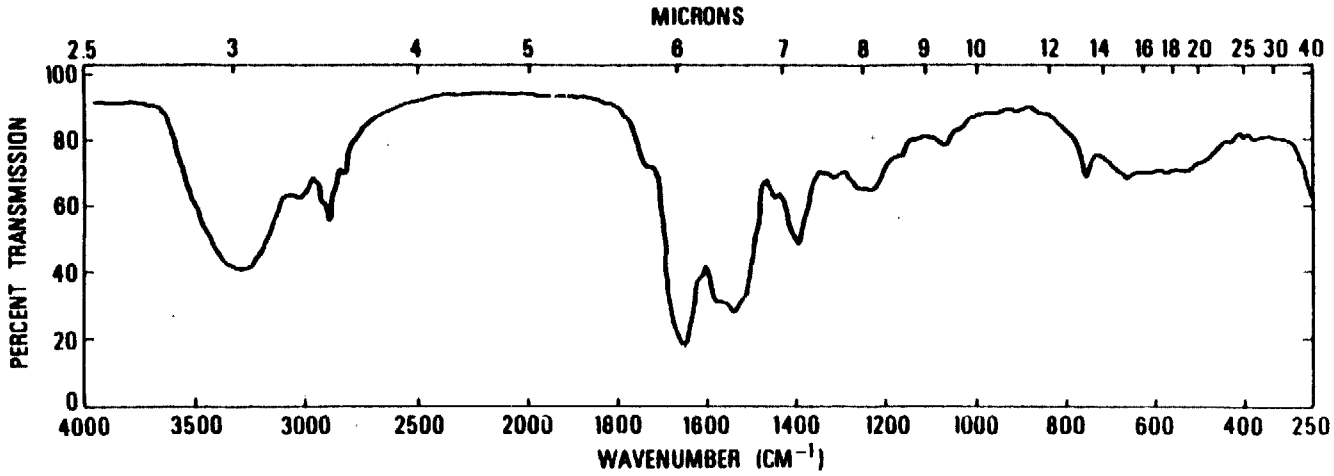
FIG. 1—A-21978C Complex
FIG. 2—A-21978C Factor $C_1$
FIG. 3—A-21978C Factor $C_2$
FIG. 4—A-21978C Factor $C_3$
FIG. 5—A-21978C Factor $C_0$
FIG. 6—A-21978C Factor $C_4$
FIG. 7—A-21978C Factor $C_5$

The A-21978C factors of this invention are closely related peptide antibiotics. As many as six antibiotic factors are recovered from the fermentation and are obtained as a mixtue, the A-21978C complex. Individual factors $C_0$, $C_1$, $C_2$, $C_3$, $C_4$ and $C_5$ are isolated as individual compounds as hereinafter described.

The A-21978C factors are closely related, acidic, cyclic polypeptide antibiotics bearing a fatty acid acyl group at the terminal amino group. Upon hydrolysis, each of the factors yielded the following amino acids:

| Amino Acid | No. of moles |
|---|---|
| Aspartic acid* | 4 |
| Glycine | 2 |
| Alanine | 1 |
| Serine | 1 |
| Threonine | 1 |
| Tryptophan | 1 |
| Ornithine | 1 |
| Kynurenine | 1 |
| 3-Methylglutamic acid** | 1 |

*one of which could be asparagine
**could be from 3-methylglutamine

Each of the A-21978C factors contains a fatty acid. Table I summarizes carbon content, and the identity where known, of the fatty acid contained by each of the A-21978C factors.

TABLE I

| A-21978C Factor | Fatty Acid: Carbon Content | Fatty Acid: Identity |
|---|---|---|
| $C_1$ | $C_{11}$ | 8-methyldecanoic acid |
| $C_2$ | $C_{12}$ | 10-methylundecanoic acid |
| $C_3$ | $C_{13}$ | 10-methyldodecanoic acid |
| $C_0$ | $C_{10}$ | — |
| $C_4$ | $C_{12}$ | — |
| $C_5$ | $C_{12}$ | — |

Subtractive Edman degradation reactions indicate that tryptophan is the N-terminal amino acid and that an aspartic acid moiety is the next adjacent amino acid.

Gas-chromatographic mass-spectral studies on A-21978C factor $C_2$ indicate that one of the two following sequences could be the structure of this factor (Asx indicates aspartic acid or asparagine and MeGlx indicates 3-methylglutamic acid or 3-methylglutamine):

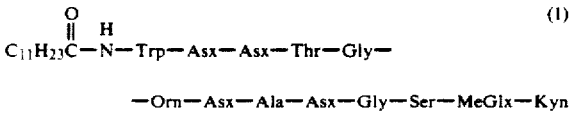

(1)

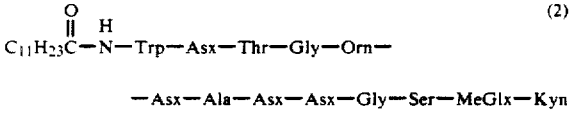

(2)

Enzymatic hydrolysis of A-21978C factor $C_2$, using carboxypeptides Y confirmed that kynurenine is the C-terminal amino acid and that the C-terminal COOH group may esterify the hydroxyl group of the threonine moiety.

[Based on the foregoing studies, the] *The structure of the A*-21978C antibiotics is believed to be as follows:

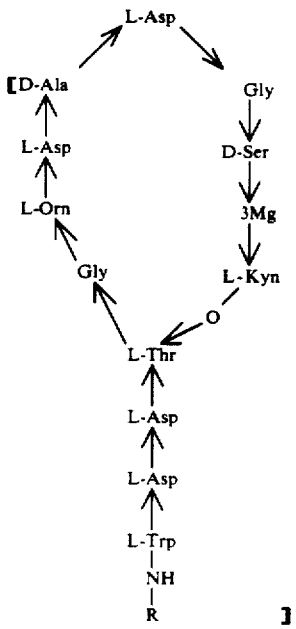

-continued

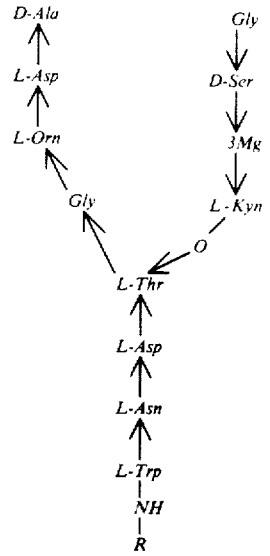

wherein 3MG represents L-threo-3-methylglutamic acid, and R represents a specific fatty acid moiety, the specific R groups of the factors being as follows:

| A-21978C Factor | R Moiety |
|---|---|
| $C_1$ | 8-methyldecanoyl |
| $C_2$ | 10-methylundecanoyl |
| $C_3$ | 10-methyldodecanoyl |
| $C_0$ | $C_{10}$—alkanoyl* |
| $C_4$ | $C_{12}$—alkanoyl* |
| $C_5$ | $C_{12}$—alkanoyl* |

Identity not yet determined

The A-21978C complex and factors (as Na salts) are soluble in water and in acidic and alkaline solutions, except at pH levels of below about pH 3.5; in lower alcohols such as methanol, ethanol, propanol, and butanol; and in dimethylformamide, dimethyl sulfoxide, dioxane, and tetrahydrofuran; but are only slightly soluble or are insoluble in acetone, chloroform, diethyl ether, benzene, ethyl acetate, and hydrocarbon solvents. The salt forms of the A-21978C complex and factors are soluble in water, methanol, dimethylformamide, and dimethyl sulfoxide; but are insoluble in solvents such as ethanol, butanol, and dioxane.

Table II summarizes the approximate percentage elemental composition of the sodium salt of each of the A-21978C factors.

TABLE II

| | A-21978C Factor | | | | | | | | | |
|---|---|---|---|---|---|---|---|---|---|---|
| | $C_0$ | | $C_1$ | | $C_2$ | | $C_4$ | $C_3$ | | $C_5$ |
| Element | Calcd | Found | Calcd | Found | Calcd | Found | Found | Calcd | Found | Found |
| Carbon | 52.61 | 52.07 | 52.89 | 52.47 | 53.17 | 51.87 | 52.73 | 53.44 | 54.18 | 52.76 |
| Hydrogen | 6.07 | 5.95 | 6.14 | 5.93 | 6.21 | 6.05 | 5.99 | 6.28 | 6.35 | 6.71 |
| Nitrogen | 13.63 | 12.73 | 13.52 | 13.38 | 13.41 | 13.66 | 14.07 | 13.29 | 13.34 | 13.97 |
| Oxygen | 26.28 | 25.84 | 26.06 | 26.19 | 25.84 | 25.86 | 25.81 | 25.63 | 25.06 | 25.60 |
| Sodium* | 1.40 | 3.41 | 1.39 | 2.03 | 1.38 | 2.56 | 1.40 | 1.36 | 1.07 | 0.96 |

*by difference

The infrared absorption spectra of the A-21978C complex and factors (as Na salts) in KBr pellet are shown in FIGS. 1–7 of the accompanying drawings. Table III summarizes the most significant absorption maxima for each of these.

TABLE III

| IR Maxima ($cm^{-1}$) of the A-21978C Complex and Factors | | | | | | |
|---|---|---|---|---|---|---|
| Complex | $C_0$ | $C_1$ | $C_2$ | $C_3$ | $C_4$ | $C_5$ |
| 3310 | 3300 | 3300 | 3310 | 3310 | 3320 | 3300 |
| 3050 | 3050 | 3040 | 3050 | 3040 | 3050 | 3045 |
| 2910 | 2910 | 2910 | 2910 | 2910 | 2920 | 2910 |
| 2840 | 2840 | 2840 | 2840 | 2835 | 2850 | 2840 |
| 1655 | 1650 | 1650 | 1665 | 1650 | 1655 | 1650 |
| 1540 | 1540 | 1535 | 1535 | 1535 | 1525 | 1525 |
| 1450 | 1445 | 1450 | 1450 | 1450 | 1455 | 1445 |
| 1395 | 1395 | 1395 | 1400 | 1395 | 1395 | 1390 |
| 1310 | | | | | | |
| 1240 | 1215 | 1220 | 1225 | 1225 | 1220 | 1215 |
| 1160 | 1155 | 1160 | 1160 | 1160 | 1160 | 1155 |
| 1065 | 1060 | 1065 | 1065 | 1060 | 1065 | 1055 |
| 745 | 745 | 745 | 745 | 745 | 740 | 735 |
| 643 | | | | | | |
| 555 | | | | | | |
| 518 | | | | | | |

The approximate weights and molecular formulas of the three major A-21978C factors are summarized in Table IV.

TABLE IV

| A-21978C Factor | Molecular Weight | | Formula | |
|---|---|---|---|---|
| $C_0$ | [1622] | *1621* | [$C_{72}H_{100}N_{16}O_{27}$] | $C_{72}H_{101}N_{17}O_{26}$ |
| $C_1$ | [1636] | *1635* | [ $_{73}H_{102}N_{16}O_{27}$] | $C_{73}H_{103}N_{17}O_{26}$ |
| $C_2$ | [1650] | *1649* | [$C_{74}H_{104}N_{16}O_{27}$] | $C_{74}H_{105}N_{17}O_{26}$ |
| $C_3$ | [1664] | *1663* | [$C_{75}H_{106}N_{16}O_{27}$] | $C_{75}H_{107}N_{17}O_{26}$ |
| $C_4$ | [1650] | *1649* | [$C_{74}H_{104}N_{16}O_{27}$] | $C_{74}H_{105}N_{17}O_{26}$ |
| $C_5$ | [1650] | *1649* | [$C_{74}H_{104}N_{16}O_{27}$] | $C_{74}H_{105}N_{17}O_{26}$ |

Table V summarizes the absorption maxima of the ultraviolet absorption spectra of the three major A-21978C factors (Na salt forms) in neutral ethanol.

TABLE V

| UV Maxima (ethanol-neutral) | | | |
|---|---|---|---|
| | $E_{1cm}^{1\%}$ | | |
| nm | $C_1$ | $C_2$ | $C_3$ |
| 223 | 307 | 303 | 300 |
| 260 | 62 | 62 | 63 |
| 280 | 39 | 41 | 42 |
| 290 | 35 | 36 | 38 |
| 360 | 33 | 33 | 32 |

Table VI summarizes the electrometric titration data, as determined in 66% aqueous dimethylformamide, for the three major A-21978C factors and the A-21978C complex (Na salt forms).

TABLE VI

| Titration (66% DMF) | |
|---|---|
| A-21978C | $pK_a$ Values* |
| Factor $C_1$** | 5.7, 5.9; 7.2, 7.6 |
| Factor $C_2$** | 5.8, 5.93; 7.6, 7.63 |
| Factor $C_3$** | 5.73, 5.75; 7.54, 7.58 |
| Complex | 5.62; 7.16 |

*All have lesser groups at 11.5–12
**Two determinations

The optical rotations of the A-21978C factors (Na salts), $[\alpha]_D^{25}$, when determined in water are summarized in Table VII.

TABLE VII

| Optical Rotations | |
|---|---|
| A-21978C Factor | Rotation |
| $C_0$ | +11.9° (c 0.7, $H_2O$) |
| $C_1$ | +16.9° (c 0.7, $H_2O$) |
| $C_2$ | +18.6° (c 0.9, $H_2O$) |
| $C_3$ | +20.9° (c 0.4, $H_2O$) |
| $C_4$ | +14.8° (c 0.7, $H_2O$) |
| $C_5$ | +17.9° (c 0.7, $H_2O$) |

The A-21978C factors may be separated by high-performance liquid chromatography (HPLC), using the following conditions:

Column: glass, 1×21 cm
Packing: silica gel/$C_{18}$(Quantum LP-1)
Solvent: water:methanol:acetonitrile (95:30:75) containing 0.2% acetic acid and 0.2% pyridine
Detector: UV at 285 nm
Pressure: 100 psi The retention times for the A-21978C factors (Na salts) are summarized in Table VIII.

TABLE VIII

| HPLC Retention Times | | |
|---|---|---|
| A-21978C Factor | Time (minutes) | Bioassay (*Micrococcus luteus*) (units/mg) |
| $C_0$ | 6 | 966 |
| $C_1$ | 8 | 1663 |
| $C_4$ | 9 | 1410 |
| $C_2$ | 13 | 1390 |
| $C_5$ | 14 | 1246 |
| $C_3$ | 19 | 803 |

The A-21978C complex can be separated and distinguished from A-21978C factors A, B, D and E by using silica-gel thin-layer chromatography (TLC). Acetonitrile:water (3:1) is a preferred solvent system, and bioautography with Micrococcus luteus is a preferred detection method. The approximate $R_f$ values of these A-21978C factors (Na salt forms) are given in Table IX.

TABLE IX

| A-21978 Factor | $R_f$ Value |
|---|---|
| A | 0.66 |
| B | 0.57 |
| C complex | 0.31 |
| D | 0.51 |
| E | 0.48 |

The factors of the A-21978C complex can be separated and distinguished from each other most conveniently using reversed-phase silica-gel TLC (Quantum, $C_{18}$). A preferred solvent system is water:methanol:acetonitrile (45:15:40) which contains 0.2 percent pyridine and 0.2 percent acetic acid. Long-wave UV light (365 nm) may be used for detection. The approximate $R_f$ values of the A-21978C factors (Na salt forms) in this system are given in Table X.

TABLE X

| A-21978C Factor | $R_f$ Value |
|---|---|
| $C_0$ | 0.71 |
| $C_1$ | 0.64 |
| $C_2$ | 0.56 |
| $C_3$ | 0.47 |
| $C_4$ | 0.63 |
| $C_5$ | 0.53 |

The A-21978C factors and the A-21978C complex are stable in solutions having a pH of 2–9 at 5° C. and 25° C. for at least seven days. They are unstable at pH 11 after four hours (total inactivation) at both 5° C. and 25° C.

The A-21978 and A-21978C complexes and individual A-21978C factors $C_0$, $C_1$, $C_2$, $C_3$, $C_4$ and $C_5$ are capable of forming salts. These salts are also part of this invention. Such salts are useful, for example, for separating and purifying the complexes and the individual factors. In addition, pharmaceutically acceptale salts are especially useful. "Pharmaceutically-acceptable" salts are those in which the toxicity of the compound as a whole toward warm-blooded animals is not increased relative to the non-salt form.

It will be appreciated that the A-21978 antibiotics have as many as five free carboxyl groups which can form salts. Partial, mixed and complete salts are, therefore, contemplated as part of this invention. In preparing these salts, pH levels greater than 10 should be avoided due to the instability of the antibiotics at such levels.

The A-21978 antibiotics also have two free amino groups and can, therefore, form mono- or di-acid-addition salts.

Pharmaceutically-acceptable alkali-metal, alkaline-earth-metal and amine salts and acid-addition salts are particularly useful. Representative and suitable alkali-metal and alkaline-earth metal salts of the A-21978 antibiotics include the sodium, potassium, lithium, cesium, rubidium, barium, calcium and magnesium salts. Suitable amine salts of the A-21978 antibiotics include the ammonium and the primary, secondary, and tertiary $C_1$–$C_4$-alkylammonium and hydroxy-$C_2$–$C_4$-alkylammonium salts. Illustrative amine salts include those formed by reaction of an A-21978 antibiotic with ammonium hydroxide, methylamine, sec-butylamine, isopropylamine, diethylamine, di-isopropylamine, ethanolamine, triethylamine, 3-amino-1-propanol and the like.

The alkali-metal and alkaline-earth-metal cationic salts of the A-21978 antibiotics are prepared according to procedures commonly used for the preparation of cationic salts. For example, the free acid form of A-21978C factor $C_1$, is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent.

The salts formed with organic amines can be prepared in a similar manner. For example, the gaseous or liquid amine can be added to a solution of A-21978C factor $C_1$ in a suitable solvent such as acetone; the solvent and excess amine can be removed by evaporation.

Representative and suitable acid-addition salts of the A-21978 antibiotics include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, sorbic, picric, benzoic, cinnamic and like acids.

It is well known in the veterinary pharmaceutical art that the form of an antibiotic is not ordinarily of great significance when treating an animal with the antibiotic. In most cases, conditions within the animal change the drug to form other than that in which it was administered. The salt form in which it may be administered is, therefore, not of great significance. The salt form may, however, be chosen for reasons of economy, convenience, and toxicity.

The novel antibiotics of this invention are produced by culturing an A-21978-producing strain of Streptomyces roseosporus under submerged aerobic conditions in a suitable culture medium until substantial antibiotic activity is produced. The antibiotics are recovered by the use of various isolation and purification procedures recognized in the fermentation art.

THE MICROORGANISM

The microorganism of this invention was studied and characterized by Frederick P. Mertz and Ralph E. Kastner of the Lilly Research Laboratories.

The new organism useful for the preparation of the A-21978C antibiotics was isolated from a soil sample collected on Mount Ararat, Turkey. This organism is classified as a novel strain of Streptomyces roseosporus, Falcão de Morias and Daliá Maia 1961. This classification is based on a comparison with published descriptions [R. E. Buchanan and N. E. Gibbons, "Bergey's Manual of Determinative Bacteriology," The Williams and Wilkins Company, 8th Ed., 1974; and E. B. Shirling and D. Gottlieb, "Cooperative Description of Type Strains of Streptomyces," Intern. Journal of Systematic Bacteriol., 808–809 (1972)].

This classification is based on methods recommended for the International Streptomyces Project [E. B. Shirling and D. Gottlieb, "Methods of Characterization of Streptomyces Species," Intern. Journal of Systematic Bacteriol. 16, 313–340 (1966)] along with certain supplementary tests. Carbon utilization was determined on ISP #9 basal medium to which carbon sources were added to equal a final concentration of 1.0%. The carbon sources were sterilized by filtration; the basal medium was sterilized by autoclaving. Plates were read after 14 days incubation at 30° C. The cell-wall sugars were determined using a modification of the procedure of Lechevalier, (M. P. Lechevalier, "Chemical Methods as Criteria for the Separation of Actinomycetes into Genera," Workshop sponsored by the Subcommittee on Actinomycetes of the American Society of Microbiology, Dr. Thomas G. Pridham, Convenor; held at the Institute of Microbiology, Rutgers University, The State University of New Jersey, New Brunswick, N.J., 1971). The isomer of diaminopimelic acid was determined using the method of Becker et al. [B. Becker, et al., "Rapid Differentiation Between Norcardia and Streptomyces by Paper Chromatography of Whole Cell Hydrolysates," Appl. Microbiol. 11, 421–423 (1964)]. Amino acid analysis was determined with washed cell-wall fragments. Melanoid pigments were determined using ISP #1 (tryptone-yeast extract broth), ISP #6 (peptone-yeast extract iron agar), ISP #7 (tyrosine agar), ISP #7 modified (ISP #7 without tyrosine), and a tyrosine assay [Yuzuru Mikami, et al., "Modified Arai and Mikani Melanin Formation Test of Streptomyces," Intern. Journal of Systematic Bacteriol. 27(3), 290(1977)]. Starch hydrolysis was determined by testing for the presence of starch with iodine.

Temperature range, NaCl tolerance, pH range, and antibiotic sensitivity were done using ISP #2 agar medium. The range of temperatures were: 25°, 28°, 30°, 34°, 37°, 40°, 45°, 50° and 55° C. NaCl tolerance was measured by adding NaCl to the agar to equal: 0, 1, 2, 3, 4, 5, 6, 8, 10 and 12%. These were incubated at 30° C. The pH range was measured by adjusting the agar from pH 3.0 to 11.0 at increments of 1.0 pH units, just prior to pouring. Antibiotic sensitivity was determined using sensitivity discs padded onto seeded agar plates.

Color names were assigned according to the ISCC-NBS method (K. L. Kelly and D. B. Judd, "The ISCC-NBS Methods of Designating Colors and a Dictionary of Color Names," U.S. Department of Commerce Circ. 553, Washington, D.C., 1955).

Figures in parentheses refer to the Tresner and Backus color series [H. D. Tresner, and E. J. Backus, "System of Color Wheels for Streptomycete Taxonomy," Appl. Microbiol. 11, 335–338 (1956)]. Color tab designations are underlined. The Maerz and Paul color blocks are enclosed in brackets (A. Maerz and M. R. Paul, "Dictionary of Color," McGraw-Hill Book Company, Inc., New York, N.Y., 1950).

CHARACTERIZATION OF A-21978-PRODUCING STRAIN

Morphology

The morphology of culture A-21978.6, the culture which produces the A-21978 antibiotics, consists of sporophores which are of the Rectus-Flexibilis (RF) classification. Spore chains have >10 spores per chain. Spore surface is smooth.

Culture A-21978.6 is characterized by the production of a predominantly red aerial spore mass color, with a reddish-borwn reverse color. A light-brown water-soluble pigment is also present. These characteristics are exhibited on three of 14 agar plating media (ISP #2, ISP #7, TPO). These three media are the only ones which supported abundant aerial and vegetative growth.

Two agar plating media, ISP #4 and glucose-asparagine agar, produced a white-to-gray aerial spore mass color, with a yellow reverse color. No water-soluble pigment was observed. These two media supported good, but not abundant, aerial and vegetative growth.

Nine other agar plating media were used, but these gave poor-to-no growth and sporulation. Aerial color when present, although poor, was in the white-to-gray color series.

Melanoid pigments are absent. Major constituents of the cell wall are: LL-DAP, glycine, glucose, and ribose. This indicates a Type I cell wall, and type C sugar pattern (R. E. Buchanan, and N. E. Gibbons, Eds., "Bergey's Manual of Determinative Bacteriology," The Williams & Wilkins Company, 8th Edition, 1974, p. 658).

The following five cultures were compared in laboratory tests to A-21978.6:

Streptomyces albovinaceous ISP 5136; ATCC 15833
Streptomyces candidus ISP 5141; ATCC 19891
Streptomyces moderatus ISP 5529; ATCC 23443
Streptomyces roseosporus ISP 5122; ATCC 23958
Streptomyces setonii ISP 5395; ATCC 25497

These cultures belong to the white and red color series, have RF type sporophore morphology, smooth spore surface ornamentation, and, according to the ISP descriptions, are melanin negative and do not have a distinctive reverse color or water-soluble pigments. These characteristics, together with carbon-utilization pattern and other secondary features, match those of culture A-21978.6.

When these cultures were compared with A-21978.6 under laboratory conditions, four were rejected. S. candidus and S. setonii exhibited a yellow aerial spore mass on many media, thereby differing from culture A-21978.6. S. albovinaceous and S. moderatus exhibited dark distinctive reverse color, water-soluble pigments, and produced melanoid pigments, all of which were different from culture A-21978.6. The ISP description of S. moderatus refers to reddish brown or strong-brown reverse color, but does not refer to such a characteristic for S. albovinaceous. Neither culture is listed as melanin positive.

Culture A-21978.6 was classified, therefore, as a strain of Streptomyces roseosporus, Falcao de Morias and Dalia Maia 1961. This classification was based on comparison with published descriptions and direct laboratory comparisons. The following cultural characteristics summarize the direct comparison studies.

CULTURAL CHARACTERISTICS

| | A21978.6 | | *S. roseosporus* |
|---|---|---|---|
| Morphology | Sporophores straight to flexuous (RF), with no hooks, loops or spirals observed. Chains of spores >10. The spore surface smooth as determined by scanning electron microscopy. | | |
| Spores: Oblong to oval<br>Average: 0.85 × 1.78 μM<br>Range: 0.65–0.97 × 0.97–2.6 μM | | Oblong to cylindrical<br>1.01 × 2.47 μM<br>0.97–1.3 × 1.63–3.25 μM | |
| Growth | Color | Growth | Color |
| Carrot Plugs | | | |
| Aerial: good | gray c̄ pink | none | none |
| Vegetative: abundant | brown | good | yellow-brown |

-continued

CULTURAL CHARACTERISTICS

Morphology

| A21978.6 | | *S. roseosporus* | |
|---|---|---|---|
| Sporophores straight to flexuous (RF), with no hooks, loops or spirals observed. Chains of spores >10. The spore surface smooth as determined by scanning electron microscopy. | | | |
| Spores: Oblong to oval | | Oblong to cylindrical | |
| Average: 0.85 × 1.78 μM | | 1.01 × 2.47 μM | |
| Range: 0.65-0.97 × 0.97-2.6 μM | | 0.97-1.3 × 1.63-3.25 μM | |
| Growth | Color | Growth | Color |
| no soluble pigment | | no soluble pigment | |
| | | Potato Plugs | |
| Aerial: good | gray c̄ pink | none | none |
| Vegetative: abundant | brown | fair | orange-brown |
| dark brown soluble pigment | | no soluble pigment | |
| | | ISP #1 (Tryptone-yeast ext. agar) | |
| Aerial: fair | (W)a white | poor | (W)a white |
| Vegetative: good | [10A1] pale yellow green | poor | [10B2] pale yellow green |
| no soluble pigment | | no soluble pigment | |
| | | ISP #2 (Yeast-malt extract agar) | |
| Aerial: abundant | (R) 5cb gy. yellow pink | abundant | (R) 3ca pale orange yellow |
| Vegetative: abundant | [5D10] lt. red brown | abundant | [12L7] lt. olive brown |
| light brown sol. pigment | | light brown sol. pigment | |
| | | ISP #3 (Oatmeal agar) | |
| Aerial: fair | (W)a white | poor | (W)a white |
| Vegetative: fair | [10A2]pale yellow pink | fair | pale greenish gray |
| light brown sol. pigment | | no soluble pigment | |
| | | ISP #4 (Inorganic salts starch agar) | |
| Aerial: good | (W)b white | good | (R) 3c2 pale orange yellow |
| Vegetative: good | [10B1] pale yellow-green | abundant | [11I5] grayish yellow |
| light brown sol. pigment | | no soluble pigment | |
| | | ISP #5 (Glycerol - asperagine agar) | |
| Aerial: fair | (W) 13ba purplish white | fair | (W) b white |
| Vegetative: good | [3B7] gy. yellow pink | good | [10C2] grayish yellow |
| gy. pink sol. pigment | | light brown sol. pigment | |
| | | ISP #7 (Tyrosine agar) | |
| Aerial: abundant | (R) 5cb gy. yell. pink | abundant | (R) 5cb gy. yell. pink |
| Vegetative: abundant | [7L12] mod. red brown | abundant | [11E5] yellow-brown |
| dark brown sol. pigment | | light brown sol. pigment | |
| | | Bennett's modified agar | |
| Aerial: none | — | abundant | (R) 5cb gy. yell. pink |
| Vegetative: poor | pale yellow br. | abundant | [11D4] grayish yellow |
| no soluble pigment | | light brown sol. pigment | |
| | | Calcium malate agar | |
| Aerial: none | — | poor | (W) a white |
| Vegetative: fair | [7L12] mod. red brown | poor | pale yellow-green |
| light brown sol. pigment | | pale yell.-green sol. pigment | |
| | | Czapek's solution agar | |
| Aerial: poor | (W)a white | none | — |
| Vegetative: poor | off-white | none | — |
| no soluble pigment | | | |
| | | Emerson's agar | |
| Aerial: poor | — | abundant | (R)5cb gy. yell. pink |
| Vegetative: abundant | [13L6] | abundant | [11I5] gy. yellow |
| no soluble pigment | | light brown sol. pigment | |
| | | Glucose - asperagine agar | |
| Aerial: good | (W)b white | fair | (W)b white |
| Vegetative: good | [12B2] gy. yellow | good | [12B2] pale yell. green |
| no soluble pigment | | no soluble pigment | |
| | | Glycerol - glycine agar | |
| Aerial: poor | — | abundant | (W)b white |
| Vegetative: abundant | [8L12] dk. gy. brown | abundant | [10G3] light yellow |
| brown soluble pigment | | light brown sol. pigment | |
| | | Nutrient agar | |
| Aerial: none | — | fair | (W)b white |
| Vegetative:poor | pale yellow-gray | good | pale yellow gray |
| no soluble pigment | | no soluble pigment | |
| | | (Tomato-paste Oatmeal agar) | |
| Aerial: abundant | (R)5cb gy. yell. pink | abundant | (R) 5cb gy. yell. pink |
| Vegetative: abundant | [8L12] dk. gy. brown | abundant | [12L7] yell. brown |
| brown soluble pigment | | brown soluble pigment | |

| Substrate | Carbon Utilization A21978.6 | *S. roseosporus* |
|---|---|---|
| L-Arabinose | + | + |
| D-fructose | + | − |
| D-Galactose | + | + |
| D-Glucose | + | + |
| i-Inositol | − | − |
| D-Mannitol | + | − |
| D-Raffinose | − | − |
| L-Rhamnose | + | + |
| Salicin | + | + |
| Sucrose | − | − |
| D-Xylose | + | + |

Key:
+ = Positive utilization
− = Negative utilization

| Characteristic | A21978.6 | *S. roseosporus* |
|---|---|---|
| Melanoid Pigments | | |
| ISP #1 (tryptone-yeast ext.) | − | − |
| ISP #6 (peptone-yeast ext. iron) | − | − |
| ISP #7 (tyrosine agar) | − | − |
| ISP #7 mod. (ISP #7 minus tyrosine) | − | − |
| Tyrosine asay | − | − |
| Gelatin liquefaction | + | + |
| Skim milk action | slight hydrolysis | slight hydrolysis |
| Starch hydrolysis | + | + |
| pH range | 5-11 | 5-11 |
| Temperature range | 25-40° C. | 25-45° C. |
| Nitrate reduction | − | + |
| NaCl tolerance growth up to | 10% | 6% |

| Antibiotic | Conc./Disc | Class | A21978.6 | *S. roseosporus* |
|---|---|---|---|---|
| Erythromycin | 15 μg | Macrolide | + | + |
| Cephalothin | 30 μg | β-Lactam | + | + |
| Lincomycin | 2 μg | Glycoside | − | − |
| Nystatin | 100 units | Polyene | − | − |
| Polymyxin B | 300 units | Peptide | + | − |
| Streptomycin | 10 μg | Aminoglycoside | + | + |
| Tetracycline | 30 μg | Tetracycline | + | + |
| Vancomycin | +μg | Glycopeptide | + | + |

+ = sensitive (zones of inhibition)
− = resistant (no zones of inhibition)

Certain characteristics of the A-21978-producing S. roseosporus NRRL 11379 strain differ from the characteristics published for S. roseosporus. Culture A-21978.6 differs from the published strain in spore size, carrot- and potato-plug growth, NaCl tolerance, and in nitrate reduction.

The Streptomyces roseosporus culture useful for the production of the A-21978 antibiotics has been deposited and made a part of the stock culture collection of the Northern Regional Research Center, U.S. Department of Agriculture, Agricultural Research Service, Peoria, Ill., 61604, from which it is available to the public under the number NRRL 11379.

As is the case with other organisms, the characteristics of the A-21978-producing culture, streptomyces roseosporus NRRL 11379, are subject to variation. For example, artificial variants and mutants of the NRRL 11379 strain may be obtained by treatment with various known mutagens such as ultraviolet rays, X-rays, high-frequency waves, radioactive rays and chemicals. All natural and artificial variants and mutants of Streptomyces roseosporus NRRL 11379 which produce the A-21978 antibiotics may be used in this invention.

The culture medium used to grow Streptomyces roseosporus NRRL 11379 can be any one of a number of media. For economy in production, optimal yield, and ease of product isolation, however, certain culture media are preferred. Thus, for example, a preferred carbon source in large-scale fermentation is tapioca dextrin, although glucose, fructose, galactose, maltose, mannose, cottonseed oil, methyl oleate, glycerol, refined soybean oil, and the like can also be used. A preferred nitrogen source is enzyme-hydrolyzed casein, although soluble-meat peptone, soybean flour, soybean hydrolysate, soybean grits, yeast, amino acids such as L-asparagine and DL-leucine, and the like are also useful. Nutrient inorganic salts which can be incorporated in the culture media are the soluble salts capable of yielding potassium, ammonium, chloride, sulfate, nitrate and like ions. Among these, $K_2SO_4$ is especially useful for antibiotic production. Molasses ash, ash dialysate and synthetic mineral mix are also useful.

For production of the A-21978 antibiotics, it is preferable to use distilled or deionized water in the fermentation medium. Some of the minerals in tap water, such as, for example, calcium and carbonate, appear to discourage antibiotic production.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (e.g., 0.2 ml/L.) of an antifoam agent such as polypropylene glycol to large-scale fermentation media of foaming becomes a problem.

For production of substantial quantities of the A-21978 antibiotics, submerged aerobic fermentation in tanks is preferred. Small quantities of the A-21978 antibiotics may be obtained by shake-flask culture. Because of the time lag in antibiotic production commonly associated with inoculation of large tanks with the spore form of the organism, it is preferable to use a vegatative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank.

The A-21978-producing organism can be grown at temperatures between about 20° and about 37° C. Optimum A-21978C production appears to occur at temperatures of about 30°-32° C.

As is customary in aerobic submerged culture processes, sterile air is dispersed through the culture medium. For efficient production of the A-21978 antibiotics the percent of air saturation for tank production should be above 20%, preferably above 30% (at 30° C., and one atmosphere or pressure).

For tank fermentation, it is preferable to maintain the pH level of the fermentation medium in a range of from about 65-7.0. This can be done by the addition of appropriate amounts of, for example, sodium hydroxide (in the early stages) and hydrochloric acid (in the later stages).

Production of the A-21978 antibiotics can be followed during the fermentation by testing samples of the broth or of extracts of the mycelial solids for antibiotic activity against organisms known to be sensitive to the antibiotics. One assay organism useful in testing these antibiotics is Micrococcus luteus. The bioassay is preferably performed by paper-disc assay on agar plates.

Following their production under submerged aerobic fermentation conditions, the A-21978 antibiotics can be recovered from the fermentation medium by methods recognized in the fermentation art. The antibiotic activity produced during fermentation of an A-21978-producing organism generally occurs in the broth. Maximum recovery of the A-21978 antibiotics is accomplished, therefore, by an initial filtration to remove the mycelial mass. The filtered broth can be purified by a variety of techniques to give the A-21978 complex. A preferred method involves extraction and precipitation to give the A-21978 complex.

Further purification and separation of the A-21978C complex and the individual A-21978C factors includes additional adsorption and extraction procedures. Useful adsorptive materials for the purification of the A-21978C complex and factors include: (1) Anion-exchange-(a) strongly basic; polystyrene; BioRad AG 1 & 2, Bio-Rex, Dowex 1 and 2, Amberlite IRA 400, 401, 410; (b) moderately basic; epoxypolyamine Bio-Rex 5, and Duolite A30B; (c) weakly basic; polystyrene or phenolic polyamine Bio-Rad AG3, Duolite A-6, A-7. Amberlite IRA 68, IR-45, IR-4B; (2) silica gel; (3) florisil; (4) polymeric adsorbents (XAD-2 and (4); (5) high porous polymer (Diaion HP-20); (6) Sephadex G-10, G-25, and G-50; Bio-Gel P-2 and P-10; (7) reversed-phase resins, silica gel/$C_{18}$ and silica gel/$C_8$; (8) carbon; (9) DEAE cellulose, DEAE Sephadex; (10) polyamide; (11) alumina; and (12) microcellulose. Sources: Bio-Rad and Bio-Bel resins—Bio Rad Laboratories, Richmond, Calif.; Amberlite and XAD resins—Rohm and Haas Co, Philadelphia, Pa.; Duolite resins—Diamond Shamrock Chemical Co, Redwood City, Calif.; Sephadex resins—Pharmacia Fine Chemicals AB, Uppsala, Sweden; Dowex resins—Dow Chemical Co., Midland, Mich.; Diaion-Mitsubishi Chemical Industries Ltd, Tokyo, Japan; XAD resins; silica gel/$C_{18}$ and silica gel/$C_8$—E. Merck, Darmstadt, Germany.

Alternatively, the culture solids, including medium constituents and mycelium can be used without extraction or separation, but preferably after removal of water, as a source of the A-21978 antibiotics. For example, after production of A-21978 antibiotic activity, the culture medium can be dried by lyophilization and mixed directly into feed premix.

Activity of the A-21978 Antibiotics

The A-21978C complex and the individual A-21978C factors used in the tests herein discussed were always in the sodium salt form.

The A-21978 and A-21978C complexes and individual A-21978C antibiotic factors $C_0$, $C_1$, $C_2$, $C_3$, $C_4$ and $C_5$ inhibit the growth of certain pathogenic organisms, particularly gram-positive bacteria. The minimal inhibitory concentrations (MIC's) at which the A-21978C factors and the A-21978C complex inhibit selected bacteria, as determined by standard agar-dilution tests, are summarized in Table XI.

TABLE XI

| Organism | MIC (μg/ml) | | | | | | |
|---|---|---|---|---|---|---|---|
| (aerobic) | Complex | $C_0$ | $C_1$ | $C_2$ | $C_3$ | $C_4$ | $C_5$ |
| *Staphylococcus aureus* 3055 | 0.13 | 1.0 | 0.5 | 0.13 | 0.06 | 0.25 | 0.13 |
| Group D *Streptoccus* 282 | 0.25 | 2.0 | 1.0 | 0.25 | 0.13 | 1.0 | 0.13 |
| *Streptococcus pyogenes* C203 | 0.13 | 0.25 | 0.13 | 0.13 | 0.25 | 0.13 | 0.06 |
| *Streptococcus pneumoniae* Park I | 0.13 | 0.5 | 0.13 | 0.25 | 0.13 | 0.5 | 0.06 |
| *Viridans Streptococcus* 9943 | 0.5 | 1.0 | 0.5 | 1.0 | 0.5 | 1.0 | 0.13 |
| *Neisseria gonorrhoeae* 111076-4 | 8.0 | NT* | 16.0 | 4.0 | 4.0 | NT | NT |

*NT = not tested

The minimal inhibitory concentrations at which A-21978C complex and the major A-21978C factors inhibit selected bacteria, as determined by standard broth-dilution tests are summarized in Table XII.

TABLE XII

| Organism (aerobic) | MIC (μg/ml) | | | |
|---|---|---|---|---|
| | Complex | $C_1$ | $C_2$ | $C_3$ |
| *Staphylococcus aureus* 3055 | 0.25 | 1.0 | 0.5 | 0.13 |
| Group D *Streptococcus* 282 | 0.25 | 2.0 | 1.0 | 0.13 |
| *Streptococcus pyogenes* C203 | 0.13 | 0.5 | 0.25 | 0.13 |
| *Streptococcus pneumoniae* Park I | 0.5 | 2.0 | 1.0 | 0.5 |
| *Viridans Streptococcus* 9943 | 8.0 | 32.0 | 16.0 | 32.0 |

In one important aspect, the A-21978C antibiotics inhibit the growth of organisms which are resistant to other antibiotics. Table XIII summarizes agar-dilution MIC values of A-21978C factors $C_0$, $C_1$, $C_2$, $C_3$, $C_4$, and $C_5$ against representative organisms, using the ICS agar-dilution techniques.

TABLE XIII

EFFECTIVENESS OF A-21978C FACTORS AGAINST CLINICAL ISOLATES

| Test Organism* | Minimum Inhibitory Concentration (μg/ml)** | | | | | |
|---|---|---|---|---|---|---|
| | A21978$C_0$ | A21978$C_1$ | A21978$C_2$ | A21978$C_3$ | A21978$C_4$ | A21978$C_5$ |
| *Staphylococcus aureus* (10) | 1.0[10] | 0.5[10] | 0.12–0.25[10] | 0.06–0.12[10] | 0.25–0.5[10] | 0.6–0.25[10] |
| *Staphylococcus epidermidis* (12) | 1–2[12] | 0.13–0.25[9] | 0.13–0.25[9],0.5 | 0.06–0.25[11],1 | 0.25–1.0[12] | 0.13–0.5[12] |
| *Streptococcus pyogenes* (7) | 0.25–5[5],32.>32 | 0.12[5],8.16 | 0.06–0.12[5],4.8 | 0.06–0.25[6],8 | 0.13[5],16.32 | 0.6[5],4.16 |
| Group D *Streptococcus* (9) | 2–4[8],>32 | 1–2[8],>16 | 0.25–0.5[8],8 | 0.12–0.25[8],4 | 0.5–1.0[8],32 | 0.13–0.25[8],>32 |
| *Streptococcus pneumoniae* (8) | 0.13–1.0[7],4 | 0.12–1.0[7],8 | 0.12[5],0.5,4[2] | 0.06–0.25[7],4 | 0.5[7],2 | 0.06[7],2 |
| *Viridans Streptococcus* (2) | 1–4[2] | 0.5,8 | 0.5,4 | 0.5[2] | 1–2[2] | 0.13–0.25[2] |
| *Neisseria gonorrhoeae* (11) | NT*** | 16->128[11] | 4->128[11] | 4->128[9] | NT*** | NT |

*The number in parenthesis = the number of isolates tested

**The number in brackets = the number of isolates having this MIC or MIC range; where there is no number in brackets, only one isolate had this MIC.

***NT = not tested

A-21978C antibiotics also inhibit the growth of certain anaerobic bacteria. Table XIV summarizes the activity of the A-21978C complex and A-21978C factors $C_1$, $C_2$ and $C_3$ against various anaerobic bacteria, using the standard agar-dilution test.

TABLE XIV

| Test Organism | MIC (mcg/ml) | | | | | | |
|---|---|---|---|---|---|---|---|
| | $C_0$ | $C_1$ | $C_2$ | $C_3$ | $C_4$ | $C_5$ | Complex |
| *Actinomyces isaelii* | 2 | 4 | 1.0 | 1.0 | 1.0 | 5.0 | 1.0 |
| *Clostridium perfringens* | 2 | 16 | 8 | 8 | 1.0 | 0.5 | 8 |
| *Clostridium septicum* | 4 | 4 | 1.0 | 1.0 | 1.0 | 0.5 | 1.0 |
| *Eubacterium aerofaciens* | 4 | 16 | 8 | 4 | 2 | 0.5 | 8 |
| *Peptococcus asaccharolyticus* | 4 | 4 | 2 | 1.0 | 1.0 | 0.5 | 1.0 |
| *Peptococcus prevoti* | 4 | 2 | 1.0 | <0.5 | 2 | 0.5 | <0.5 |
| *Peptostreptococcus anaerobius* | 0.25 | 2 | 1.0 | 1.0 | 0.25 | 0.25 | 1.0 |
| *Peptostreptococcus intermedius* | 2 | 4 | 1.0 | <0.5 | 1.0 | 0.25 | 1.0 |
| *Propionibacterium acnes* | 1 | 8 | 2 | 1.0 | 0.5 | 0.25 | 2 |
| *Bacteroides fragilis* | >128 | >128 | >128 | >128 | >128 | >128 | >128 |
| *Fusobacterium symbiosum* | 4 | >128 | >128 | 16 | 4 | 2 | >128 |
| *Fusobacterium necrophorum* | 2 | 64 | 64 | 32 | 4 | 0.5 | >128 |

The A-21978C factors have shown in vivo antimicrobial activity against experimental bacterial infections. When two doses of test compound were administered to mice in illustrative infections, the activity observed was measured as an $ED_{50}$ value [effective dose in mg/kg to protect fifty percent of the test animals: See Warren Wick, et al., J. Bacteriol. 81, 233–235 (1961)]. The $ED_{50}$ values observed for A-21978C complex and A-21978C factors $C_1$, $C_2$, $C_3$, $C_0$, $C_4$, and $C_5$ are given in Table XV.

TABLE XV

COMPARATIVE IN VITRO AND IN VIVO ACTIVITY

| Antibiotic | *Staphylococcus aureus* | | *Streptococcus pyogenes* | | | *Streptococcus pneumoniae* | |
|---|---|---|---|---|---|---|---|
| | MIC[1] | $ED_{50}$[2] | MIC | $ED_{50}$[3] | $ED_{50}$[3] | MIC | $ED_{50}$[2] |
| A21978C$C_1$ | 0.5 | 0.22 | 0.13 | 0.064 | 93 | 0.13 | 0.3 |
| A21978$C_2$ | 0.13 | 0.16 | 0.13 | 0.032 | 59 | 0.13 | 0.14 |
| A21978$C_3$ | 0.06 | 0.08 | 0.06 | 0.032 | 66 | 0.03 | 0.09 |
| A21978$C_0$ | | | 0.25 | 0.16 | | 0.5 | 0.88 |
| A21978$C_4$ | | | 0.13 | 0.10 | | 0.5 | 0.36 |
| A21978$C_5$ | | | 0.06 | 0.053 | | 0.06 | 0.17 |
| A21978C complex | 0.13 | 0.18 | <0.03 | 0.043 | | 0.13 | 0.1 |
| Erythromycin | 0.13 | 0.5 | 0.13 | 0.64 | | 0.5 | 7.3 |

[1]MIC = minimum inhibitory concentration (μg/ml), agar dilution
[2]subcutaneous administration
[3]oral administration In an important aspect of this invention, the A-21978C factors and A-21978C complex are effective in the treatment of pyelonephritis. For example, in an experimental descending pyelonephritis infection in rats, the A-21978C factors afforded protection which was superior to that provided by vancomycin. In this test, the bacterial culture used was Streptococcus faecalis (Guze). The culture was grown on Trypticase soy agar (BBL), suspended in brain heart infusion broth (BBL), divided into 0.2-ml portions, and frozen in liquid nitrogen. Bacterial suspensions for rat inoculations were prepared daily by seeding a 50-ml flask of trypticase soy broth (BBL) from a frozen ampoule and growing the culture overnight at 37° C. on a shaker. The S. faecalis culture was diluted to $5\times10^8$ colony-forming units per ml. Test compounds were injected subcutaneously once daily for seven days. All compounds were suspended in 0.125% carboxymethylcellulose.

The experimental rat infections were accomplished by the following procedure. Female, random-bred albino rats (Cox-Wistar) weighing 190 to 210 g were anesthetized by intraperitoneal injection of 12 mg of sodium methohexital supplemented as necessary. The experimental pyelonephritis model was based on the studies of Guze and Beeson in which the left ureter was occluded for 20 min, followed by injection of 0.5 ml of the test organism in the femoral vein. Antimicrobial therapy was commenced 4 to 5 hrs postinfection. Four hours after the last treatment the rats were sacrificed, and the left kidney was removed and homogenized in a Duall grinder containing 9 ml of physiological saline. This represented a $10^{-1}$ dilution of the kidney tissue. Additional 10-fold dilutions in saline were based on the anticipated bacterial cells present in the tissue homogenate. Finally, duplicate agar pour plates were made from several of these dilutions, and the plates were incubated overnight at 37° C. The therapeutic results were expressed in two ways: (i) the percentage of rats with kidney counts of less than $10^2$ per g of kidney tissue, referred to as "cures," and (ii) the percentage of rats with at least a 4-$\log_{10}$ reduction in bacterial titer compared with infected control kidneys. Control rats were treated with 0.125% carboxymethylcellulose only. Viable cell counts in kidney tissue from control rats with S. faecalis ranged from $1.2\times10^8$ to $4.6\times10^8$ per g of homogenized tissue.

The results of these studies are summarized in Table XVI.

TABLE XVI

STREPTOCOCCUS FAECALIS DESCENDING RAT PYELONEPHRITIS TEST

| Antibiotic Tested | MIC[1] (μg/ml) | Rat Dose[2] mg/kg × 7 | Percent of Rats with a 4-Log Titer Decrease | Percent of Rats Cured |
|---|---|---|---|---|
| Vancomycin | 1.0 | 12.0 | 55 | 33 |
| A21978$C_1$ | 1.0 | 1.0 | 50 | 50 |
| A21978$C_2$ | 0.25 | 1.0 | 100 | 89 |
| A21978$C_3$ | 0.13 | 1.0 | 78 | 78 |

TABLE XVI-continued

STREPTOCOCCUS FAECALIS DESCENDING RAT PYELONEPHRITIS TEST

| Antibiotic Tested | MIC[1] (μg/ml) | Rat Dose[2] mg/kg × 7 | Percent of Rats with a 4-Log Titer Decrease | Percent of Rats Cured |
|---|---|---|---|---|
| A21978C complex | 0.25 | 1.0 | 89 | 89 |

[1]In vitro susceptibility of the *S. faecalis* Guzo strain
[2]Subcutaneous administration Toxicity data for the major A-21978C factors and the A-21978C complex are summarized in Table XVII.

TABLE XVII

TOXICITY OF A-21978C

| | $LD_{50}$(mg/kg) | | |
|---|---|---|---|
| | Mouse | | Rat |
| A-21978C | IV | SC | IV |
| Factor $C_1$ | >250 | >365 | 479 ± 32 |
| Factor $C_2$ | 150–250 | 175 | 204 ± 17 |
| Factor $C_3$ | <50 | 70–75 | <160 |
| Complex | 150 | 175–190 | 169 ± 10 |

When A-21978C complex or an A-21978C factor is used as an antibacterial agent, it may be administered either orally or parenterally. As will be appreciated by those skilled in the art, the A-21978C complex or factor is commonly administered together with a pharmaceutically acceptable carrier or diluent. The dosage of A-21978C complex or factor will depend upon a variety of considerations, such as, for example, the nature and severity of the particular infection to be treated. Those skilled in the art will recognize that appropriate dosage ranges and/or dosage units for administration may be determined by considering the MIC and $ED_{50}$ values and toxicity data herein provided together with factors such as the patient or host and the infecting microorganism.

The A-21978C antibiotics also useful as growth-promoting agents in animals. In chickens, for example, the A-21978C complex improved with weight gains and feed efficiency. Table XVIII summarizes the results of two tests demonstrating this activity. In these tests the A-21978C complex was given to animals at a concentration of 25 grams per ton of feed. The antibiotic was fed to four replicates of eight birds each in a time-replicated study conducted in batteries (total of eight replicates of eight birds, or 64 birds). The test period was the 21-day period from 7–28 days of age of the birds. The growth-performance data (weight gain, feed consumption and feed efficiency) were compared to that of 40 replicates of a contemporary control treatment.

TABLE XVIII

| Expt. | Treatment. | Conc., (g/ton) | Wt. Gain, (g) | % Impr.[1] | Feed Conc., (g) | Feed/Gain | % Impr. |
|---|---|---|---|---|---|---|---|
| 1 | Control | — | 414 | — | 734 | 1.773 | — |
| | A21978C | 25 | 431 | 4.10 | 750 | 1.741 | 1.80 |
| 2 | Control | — | 423 | — | 704 | 1.665 | — |
| | A21978C | 25 | 432 | 2.12 | 683 | 1.582 | 4.99 |

[1] $\frac{\text{treatment mean}}{\text{control mean}} \times 100 = \%$ improvement The A-21978 antibiotics are typically effective in promoting growth in poultry when administered with the animals' feed at rates of from about one to about 100 grams of A-21978 antibiotic per ton of animal feed.

In order to illustrate more fully the operation of this invention, the following examples are provided.

EXAMPLE 1

A. Shake-flask Fermentation of A-21978C

A lyophilized pellet of Streptomyces roseosporus NRRL 11379 was dissolved in 1–2 ml of sterilized water. This solution was used to inoculate an agar slant having the following composition:

| Ingredient | Amount (%) |
|---|---|
| Glucose | 0.5 |
| Yeast extract | 0.2 |
| $CaCO_3$ | 0.3 |
| Agar | 2.0 |
| Vegetable juice* | 20.0 |
| Deionized water | |

Unadjusted pH 6.1:
post-autoclaving pH 5.9
*V/8 Juice. Campbell Soup Co.

The inoculated slant was incubated at 30° C. for about seven to ten days. The mature slant culture was covered with sterile distilled water (10 ml) and scraped with a sterile pipette to loosen the spores. A portion (1 ml) of the resulting suspension of spores was used to inoculate 50 ml of a vegetative medium having the following composition:

| Ingredient | Amount (%) |
|---|---|
| Trypticase Soy Broth* | 3.0 |
| Dextrin | 2.5 |
| Water (deionized) | |

*Baltimore Biological Laboratories. Cockeysville, Md.

The inoculated vegetative medium was incubated in a 250-ml Erlenmeyer flask at 30° C. for about 48 hours on a shaker rotating through an arc two inches in diameter at 250 RPM.

This incubated vegetative medium (0.5 ml) was used to inoculate 50 ml of a production medium having the following composition:

| Ingredient | Amount (g/l) |
|---|---|
| Glucose | 7.5 |
| Tapioca dextrin* | 30.0 |
| Enzymatic hydrolysate of casein** | 5.0 |
| Enzyme-hydrolyzed casein*** | 5.0 |
| $K_2SO_4$ | 17.4 |
| L-Asparagine, anhydrous | 1.32 |
| Deionized water | q.s. 1 liter |

*Stadex 11, A. E. Staley, Co., Decatur Ill.
**NZ Amine A. Sheffield Chemical Co., Norwich, N.Y.
***Amber EHC. Amber Laboratories. Juneau. Wisc.

The inoculated production medium was incubated in a 250-ml Erlenmeyer flask at 30° C. for 6–7 days on a shaker rotating through an arc two inches in diameter at 250 RPM.

B. Tank Fermentation of A-21978C

In order to provide a larger volume of inoculum, 10 ml of incubated vegetative medium prepared as described above was used to inoculate 400 ml of a second-stage vegetative growth medium having the same composition as that of the vegetative medium. This second-stage medium was incubated in a 2-liter flask for 48 hours at 30° C. on a shaker rotating through an arc 2 inches in diameter at 250 RPM.

Incubated second-stage vegetative medium (800 ml) thus prepared was used to inoculate 100 liters of sterile production medium having the same composition given in Sect A. The inoculated production medium was allowed to ferment in a 165-liter fermentation tank for about 6–8 days at a temperature of 30° C. The fermentation medium was aerated with sterile air at a pressure of one atmosphere to maintain an air saturation of above 30%, stirring with conventional agitators at 200–300 RPM.

EXAMPLE 2

Separation of A-21978C Antibiotic Complex

Whole fermentation broth (1600 gal.), obtained as described in Example 1, was filtered on a filter press, using 3% filter aid (Celite 545, Johns-Manville Products Corp.). The filter cake was washed with water to yield a total filtrate of 4100 liters assaying 230 units/ml. The pH of the filtrate was adjusted to 3.5 with HCl, and the acidified filtrate was held at room temperature for 16 hours to allow the active factors to precipitate. Filter aid (0.75% Celite 545) was added to the suspension; the precipitate was separated by filtration. The filter cake was extracted twice with 410 liters of methanol, stirring each time for 1 hour before filtering. To the combined methanol extracts (720 liters) was aded 0.1 volume of water (72 liters). The pH of this solution was adjusted to 6.5–7.0 with NaOH. The solution was concentrated under vacuum to about 1/20th volume (30 liters) to remove the methanol; distilled water was added as needed during the concentration, n-Butanol (¾ volume or 22 liters) was added with stirring. The pH of the resulting solution was adjusted to 3.0 with HCl. The phases were separated; and the n-butanol phase, which contained the activity, was concentrated under vacuum to a residue. This residue was dissolved in a minimal amount of methanol; the methanol solution was added to 30 volumes of acetone to precipitate the major portion of the A-21978C complex. The precipitate was separated by filtration and dried to yield 247 g of crude A-21978C complex (780 units/mg).

The methanol-acetone filtrate containing the remaining portion of the A-21978 complex (factors A and B) was concentrated to a residue. The residue was dissolved in t-butanol:$H_2O$ (5:1), and this solution was freeze-dried to yield 169 g of A-21978 complex.

EXAMPLE 3

A. Purification of the A-21978C Complex

Crude A-21978C complex (734 g), prepared as described in Example 2, was suspended in water (25 liters); the pH of this suspension was adjusted to 6.5 with 5N NaOH to completely dissolve the material. This solution was applied to a column coating 27 liters of ion-exchange (acetate cycle) resin (IRA68, Rohm & Haas Co.). The column was washed with 4 column volumes of water (108 liters), and then with 5 column volumes of B 0.1N acetic acid (135 liters). The active material was eluted with 0.5N acetic acid, collecting ca. 120-liter fractions and assaying each fraction for biological activity.

The highly active fractions were combined and freeze-dried to yield 278 g of brown-colored A-21978C complex (1100 units/mg); the fractions with low activity were combined to yield 238 g of brown A-21978C complex (880 units/mg).

B. Further Purification of A-21978C Complex

A portion of the more active A-21978C complex preparation (150 g) from the IRA-68 column was suspended in water (600 ml); the pH was adjusted to 6.5 to completely dissolve the suspended preparation; a sufficient amount of dry silica gel (Grace, Grade 62) was added to absorb the aqueous solution. This moist silica-gel preparation was placed on a 30-liter silica-gel (Grace 62) column (10×375 cm) packed in acetonitrile (the silica gel had been previously washed with water to remove fine particles; the column was then packed with the silica gel suspended in water; and the silica gel column was washed with 30 liters of acetonitrile). After loading, the column was washed with acetonitrile (15 liters), and then was developed with acetonitrile:water (4:1), collecting about 4-liter fractions. Elution was monitored by bioassay and silica-gel TLC [$CH_3CN$:$H_2O$(3:1)] bioautogram. Fractions containing only A-21978C complex (fractions 43–60) were combined, concentrated under vacuum, and freeze-dried to yield 86.2 g of yellow-tan purified A-21978C complex (1160 units/mg). Fractions 21–29, containing factors D and C were combined and freeze-dried to yield 13 g of yellow powder with low biological activity.

The purified A-21978C complex (30 g) thus obtained was further decolorized by suspending 30 g of the complex in a minimal amount of water and mixing with a small amount of silica gel (Type LP-1, 10–20 microns, Quantum Industries, 341 Kaplan Drive, Fairfield, N.J. 07006) to absorb the solution. The moist silica-gel mixture was suspended in acetonitrile:methanol (4:1) and packed in a 4-×30-cm (O.D.) glass lead column attached to a 6.5×82-cm (O.D.) glass column containing 2.8 liters of silica gel (Quantum LP-1) packed in acetonitrile:methanol (4:1) [the silica gel was washed previously with water and then acetonitrile:methanol (4:1); and the column was packed with the silica gel in acetonitrile:methanol (4:1) under 50–60 psi of pressure]. The lead column and main column were washed with 3 liters of acetonitrile:methanol (4:1) at 50 psi. The active material was eluted with acetonitrile:methanol:water (55:20:25), collecting 300-ml fractions. Elution was monitored by bioassay (Micrococcus luteus). Fractions 14–25 had the highest activity and were combined, concentrated, and freeze-dried to yield 24 g of light-yellow, pure A-21978C complex as the sodium salt (1250 units/mg). Fractions 26–32 were less active; they were combined, concentrated, and freeze-dried to yield 1.6 g of less-pure A-21978C complex (780 units/mg).

EXAMPLE 4

Separation of A-21978C Factors

Purified A-21978C complex (2 g), obtained as described in Example 3, was dissolved in water (40 ml) and applied through a pump (FMI LAB Pump, Fluid Metering, Inc. 48 Summit St., Oyster Bay, N.Y. 11771) at 50 psi onto a 4.1-×60-cm column of revrese-phase silica gel (Quantum LP-1 silica gel/$C_{18}$) set in water:methanol:acetonitrile (100:15:85) containing 0.15% acetic acid and 0.15% pyridine. The column was developed at 65 psi with this solvent, collecting 25-ml fractions. Elution of factors was monitored by UV at 280 nm and by bioassay. Individual fractions were assayed on an analytical column for factor purity. Typical separations were: fractions 33-37 contained factor $C_0$; fractions 45-53 contained factor $C_1$; fractions 75-92 contained factor $C_2$; fractions 112-134 contained factor $C_3$; fractions 54-74 contained factors $C_1$, $C_2$, and $C_4$; and fractions 93-111 contained factors $C_2$, $C_3$, and $C_5$. Fractions containing mixtures were rerun on the column to obtain further yields of $C_1$, $C_2$, and $C_3$, as well as factors $C_4$ and $C_5$. The fractions containing a single factor were combined, concentrated under vacuum, and freeze-dried to give light yellow powders of each of the factors (as Na salts). From 60 g of complex the yields were: factor $C_1$=5.55 g; factor $C_2$=10 g; factor $C_3$=6.61 g. The fractions containing mixed factors were recycled over the reversed-phase resin column to give additional yields: factor $C_0$=550 mg; factor $C_1$=1.29 g; factor $C_2$=1.99 g; factor $C_3$=443 mg; factor $C_4$=512 mg; and factor $C_5$=384 mg.

EXAMPLE 5

Large-Scale Separation and Purification of A-21978C Factors

On a larger scale, the factors were separated by reverse-phase column chromatogrpahy. Pure A-21978C complex (6 g), obtained as described in Example 3, was dissolved in water (80 ml). The pH of this solution was adjusted to 4.4 with acetic acid, and tetrahydrofuran (20 ml) was added. The solution was pumped under low pressure (Lapp Pump) onto a steel column (4.8×100 cm) containing 1.77 liters of silica gel/$C_{18}$ [Quantum LP-1, 10-20 microns, silylated with octadecyltrichlorosilane] packed in water:tetrahydrofuran (THF) (4:1). The column was washed under pressure (about 100 psi) with 10 ml of $H_2O$:THF (4:1). The column was developed with water:methanol:acetonitrile (47.5:15:37.5) containing 0.2% pyridine and 0.2% acetic acid at about 100 psi at a flow rate of 35 ml/minute, collecting 175-ml fractions. Elution was monitored continuously on a recorder with an ultraviolet (uv) detector at 280 nm. Fractions containing individual factors as indicated by the peaks on the graph were further monitored on an analytical reversed-phase resin column. Fractions containing a single factor were combined and freeze-dried. A typical run is illustrated here: fractions 12-16 contained factor $C_0$; fractions 20-26 contained factor $C_1$, fractions 38-50 contained factor $C_2$; fractions 63-78 contained factor $C_3$. Fractions 27-37 (containing factors $C_1$ and $C_4$) and fractions 51-62 (containing factors $C_2$ and $C_5$) were recycled through the column to obtain pure factors $C_4$ and $C_5$. Column loads ranged from 6-12 g. Yields from a total of 84 g of A-21978C complex were: 1.9 g of $C_0$, 3.27 g of $C_1$, 497 g of $C_2$, and 1.94 g of $C_3$. Higher yields of individual factors were obtained by recycling mixed-factor fractions using appropriate HPLC solvent systems. The choice of system varied and was dependent on individual lots, and on the reverse-phase resin and columns.

The following are useful systems for separation of the A-21978C factors:

A. Analytical Systems

Water:methanol:acetonitrile (50:15:35) containing 0.2% acetic acid (HOAc) adjusted to pH 5.5 with pyridine Water:methanol:acetonitrile (50:15:35) containing 0.2% HOAc and 0.2% pyridine Water:methanol:acetonitrile (50:15:35) containing 0.75% ammonium formate Water:methanol:acetonitrile (95:30:75) containing 0.2% HOAc and 0.2% pyridine Water:methanol:acetonitrile (105:15:80) containing 0.2% HOAc and 0.2% pyridine Water:methanol:THF (59:15:25) containing 0.5% HOAc and 0.5% pyridine Water:methanol:THF (60:15:25) containing 0.5% ammonium formate.

B. Preparative Systems

Water:methanol:acetonitrile (95:20:85) containing 0.15% HOAc and 0.15% pyridine

Water:methanol:acetonitrile (100:15:85) containing 0.15% HOAc and 0.15% pyridine Water:methanol:acetonitrile (50:10:40) containing 0.1% HOAc and 0.1% pyridine Water:methanol:acetonitrile (50:15:35) containing 0.75% ammonium formate water:methanol:acetonitrile (55:10:35) containing 0.2% HOAc and 0.8% pyridine Water:methanol:THF (52.5:15:32.5) containing 0.6% ammonium formate Water:methanol:THF (50:15:35) containing 0.6% ammonium formate The advantage of acetic acid-pyridine over ammonium formate is that the former can be removed during the freeze-drying, whereas ammonium formate must be removed by column chromatography (Sephadex G-25).

EXAMPLE 6

Alternate Isolation of A-21978C Complex

Whole fermentation broth (97 liters), obtained as described in Example 1, was filtered with a filter aid (4% Hyflo Super-Cel); the resulting filtrate (80 liters) was stirred with 2 liters of a nonionic macroporous copolymer of styrene cross-linked with divinylbenzene (Diaion HP-20 resin, Mitsubishi Chemical Industries Limited, Tokyo, Japan) for 2 hours. The supernate was decanted; the resin was washed with water (8 liters); the water was decanted. The resin was then stirred with 8 liters of acetonitrile:water (15:85) for 15 minutes; the solvent was removed by filtration. The A-21978C complex was then eluted from the resin by stirring it with 8 liters of acetonitrile:water (2:3) for 1 hour and filtering. This procedure was repeated to remove all the A-21978C complex. The two filtrates were combined and concentrated in vacuo to an oil. The oil was dissolved in a minimal volume of water; two volumes of methanol were added with warming; then 30 volumes of acetone were added to precipitate the A-21978C complex. The precipitate was separated by filtration and dried in vacuo to yield 13.6 g of crude A-21978C complex (570 units/mg).

The crude A-21978C complex was purified by silica-gel column chromatography. The complex (1 g) was dissolved in a minimal volume of water; silica gel (Grace 62) was added to absorb the water; the absorbent was slurried in acetonitrile. This slurry was applied to a 1.5-×40-cm column of silica gel (Grace, Grade 62)

packed in acetonitrile. The column was then washed with acetonitrile. The activity was eluted with acetonitrile:water (4:1), collecting 25-ml fractions. Fractions were monitored as described in Example 3. Fractions 21 to 46, containing most of the A-21978C complex, were combined, concentrated to a small volume under vacuum and freeze-dried to yield 605 mg of purified A-21978C complex (Na salt) (900 units/mg).

EXAMPLE 7

Preparation of the A-21978C Complex (Acid Form)

A-21978C complex in the Na salt form (7 g), prepared as described in Example 6 was dissolved in water (150 ml); n-butanol (150 ml) was added. The pH of the mixture was adjusted to pH 3.4 with 2N HCl, while stirring for 1 hour. The n-butanol phase was separated and concentrated to a residue in vacuo. The residue was dissolved in water and freeze-dried to yield 6 g of A-21978C complex (acid form). The individual A-21978C factor salts are converted to the corresponding acid forms by the same method.

EXAMPLE 8

Preparation of A-21978C Complex Sodium Salt from A-21978C Complex in the Acid Form A-21978C complex in the acid form (50 mg), prepared as described in Example 7, was dissolved in warm absolute ethanol (5 ml); 1N NaOH was added dropwise until the pH of the solution was 9.4; the resulting solution was held at room temperature overnight. The precipitate which formed was filtered off and dried in vacuo to give 32 mg of A-21978C complex (sodium salt). The salt contained 8% sodium by atomic-absorption assay.

EXAMPLE 9

Using the procedure described in Example 8, A-21978C complex calcium salt was formed by adding $CaCl_2$ in ethanol to an ethanolic solution of A-21978C complex in the acid form.

EXAMPLE 10

Microbiological Assay for A-21978 Fermentation and Isolation Samples

The method used to quantitate the activity of A-21978 in fermentation broths and isolation samples was a paper-disc agar-diffusion system, using Micrococcus luteus.

Seeded agar-diffusion plates were prepared by inoculating a nutrient agar medium with an appropriate concentration of the test culture, pouring 8 ml agar into each 20-×100-mm plastic petri dish.

The assay reference standard was a preparation of A-21978C complex. This preparation was used on a unit basis. Highly purified A-21978C complex contains about 1250 units per milligram. The standard dose response curve was prepared to contain 150-75-40-20-10 units per ml. Diluent for the standard and samples was 0.1M pH 6.0 phosphate buffer.

Sample and standard solutions were delivered to 12.7-mm paper discs with an automatic pipette. Incubation was at 30° C. for 16–18 hrs. Zones were read on a modified Fischer-Lilly Antibiotic Zone Reader.

Figure 5:
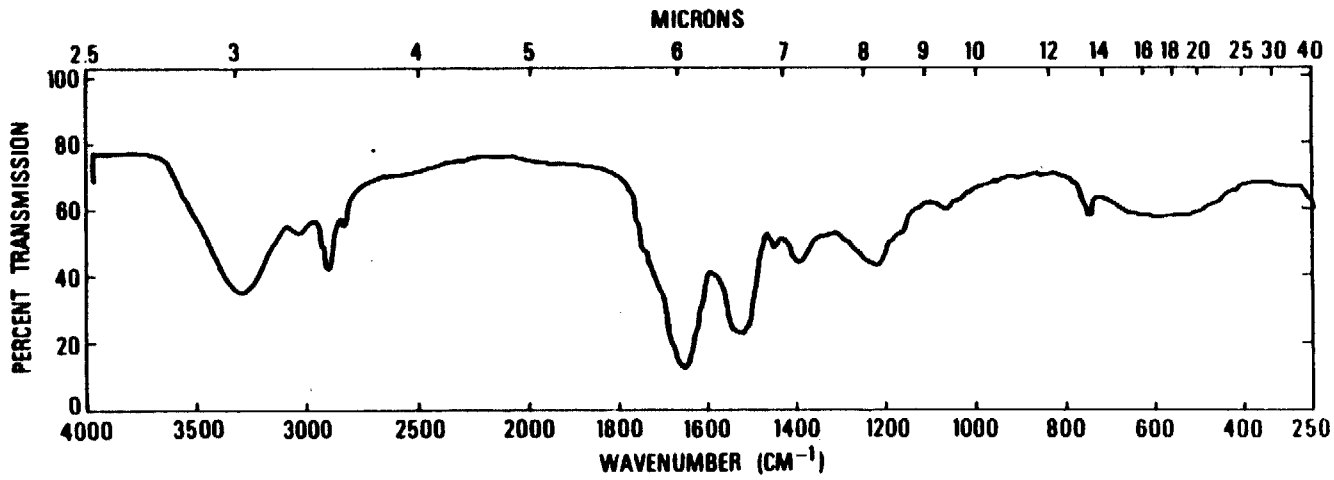

We claim:

1. Antibiotic A-21978C factor $C_0$, which has the following structural formula:

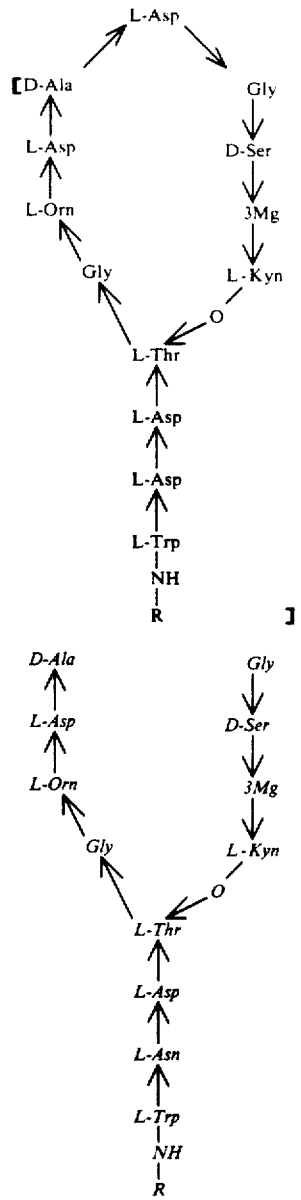

wherein 3MG represents L-threo-3-methylglutamic acid, and R is a $C_{10}$-alkanoyl moiety; and which has:

(a) a molecular formula of approximately [$C_{72}H_{100}N_{16}O_{27}$:] $C_{72}H_{101}N_{17}O_{26}$;

(b) a molecular weight of approximately [1622] *1621*; and which, in sodium salt form, has these characteristics;

(c) an approximate elemental composition of 52.07% carbon, 5.95% hydrogen, 12.73% nitrogen, 25.84% oxygen and 3.4% sodium;

(d) an infrared absorption spectrum in KBr pellet as shown in FIG. 5 of the drawings;

(e) upon hydrolysis yields the following amino acids: aspartic acid, glycine, alanine, serine, threonine, tryptophan, ornithine, kynurenine, and 3-methylglutamic acid;

(f) is soluble in methanol, ethanol, propanol, butanol, dimethylformamide, dimethyl sulfoxide, dioxane, tetrahydrofuran, and water and in acidic and alkaline solutions, except at pH levels of below about pH 3.5; but is only slightly soluble or is insoluble in acetone, chloroform, diethyl ether, benzene, ethyl acetate, and hydrocarbon solvents;

(g) an $R_f$ value of approximately 0.71 on reversed-phase silica-gel TLC in water:methanol:acetonitrile (45:15:40) which contains 0.2% pyridine and 0.2% acetic acid; and (h) the following specific rotation: $[\alpha]_D^{25}+11.9°$ (c 0.7, $H_2O$);

or a cationic or acid addition salt of A-21978 factor $C_0$.

2. A compound of claim 1 which is a pharmaceutically acceptable salt of A-21978C factor $C_0$.

3. The compound of claim 1 which is A-21978C factor $C_0$ sodium salt.

4. Antibiotic A-21978C factor $C_1$, which has the following structural formula:

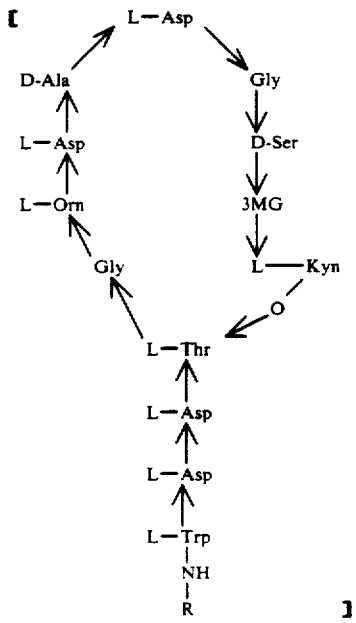

-continued

Figure 2:
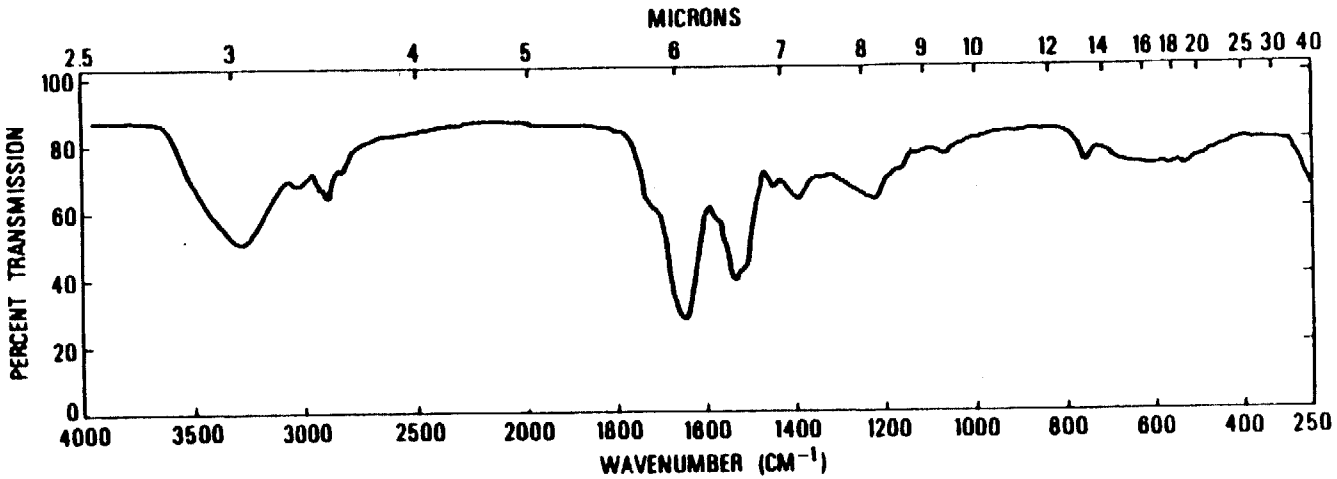

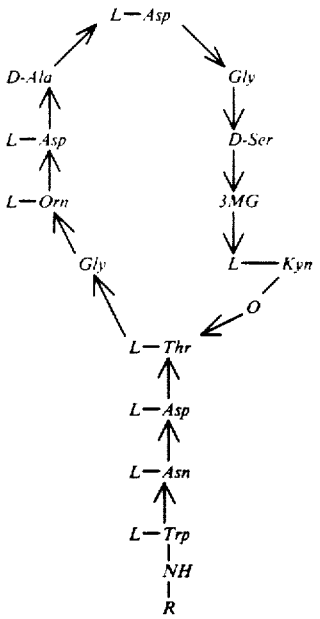

wherein 3MG represents L-threo-3-methylglutamic acid, and R is 8-methyldecanoyl; and which has:

(a) an approximate molecular formula of [$C_{73}H_{102}N_{16}O_{27}$] $C_{73}H_{103}N_{17}O_{26}$;

(b) an approximate molecular weight of [1636] *1635*; and which, in sodium salt form, has these characteristics:

(c) an approximate elemental composition of 52.47% carbon, 5.93% hydrogen, 13.38% nitrogen, 26.19% oxygen and 2.03% sodium:

(d) an infrared absorption spectrum in KBr pellet as shown in FIG. 2 of the drawings:

(e) upon hydrolysis yields the following amino acids: aspartic acid, glycine, alanine, serine, threonine, tryptophan, ornithine, kynurenine, and 3-methylglutamic acid;

(f) is soluble in methanol, ethanol, propanol, butanol, dimethylformamide, dimethyl sulfoxide, dioxane, tetrahydrofuran, and water and in acidic and alkaline solutions, except at pH levels of below about pH 3.5; but is only slightly soluble or is insoluble in acetone, chloroform, diethyl ether, benzene, ethyl acetate, and hydrocarbon solvents;

(g) an $R_f$ value of approximately 0.64 on reversed-phase silica-gel TLC in a water:methanol:acetonitrile (45:15:40) which contains 0.2% pyridine and 0.2% acetic acid;

(h) the following specific rotation: $[\alpha]_D^{25}+16.9°$ (c 0.7, $H_2O$);

(i) an ultraviolet absorption spectrum in neutral ethanol with maxima at 223 ($E^{1\%}_{1\,cm}$307), 260 ($E^{1\%}_{1\,cm}$62), 280 ($E^{1\%}_{1\,cm}$39), 290 ($E^{1\%}_{1\,cm}$35), and 360 nm ($E^{1\%}_{1\,cm}$33); and (j) two titratable groups in 66% aqueous dimethylformamide with $pK_a$ values of approximately 5.8 and 7.4; or a cationic or acid addition salt of A-21978C factor $C_1$.

5. A compound of claim 4 which is a pharmaceutically acceptable salt of A-21978C factor $C_1$.

6. The compound of claim 4 which is A-21978C factor $C_1$ sodium salt.

7. Antibiotic A-21978C factor $C_2$, which has the following structural formula:

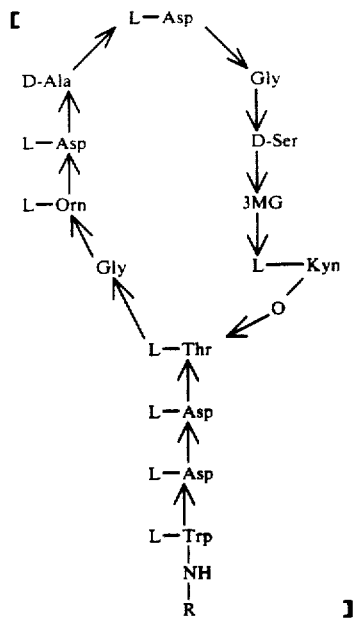

Figure 3:
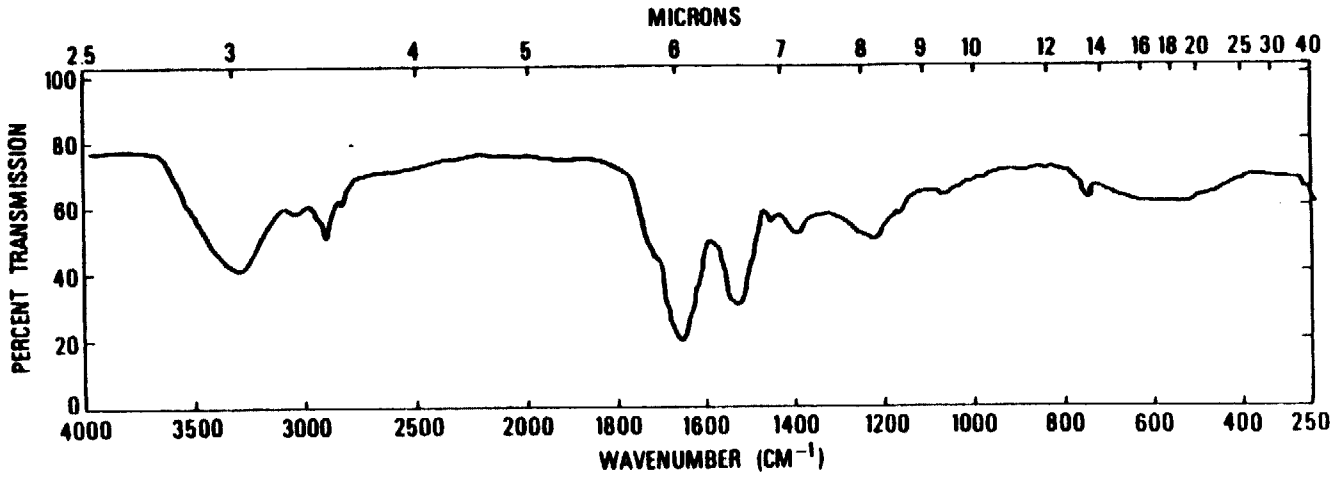

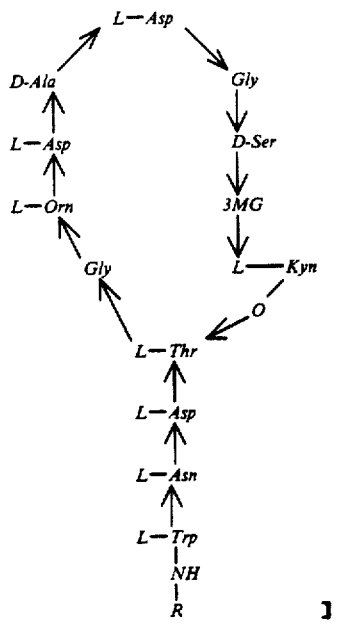

wherein 3MG represents L-threo-3-methylglutamic acid, and R is 10-methylundecanoyl; and which has:

(a) an approximate molecular formula of [$C_{74}H_{104}N_{16}O_{27}$] $C_{74}H_{105}N_{17}O_{26}$;

(b) an approximate molecular weight of [1650] *1649*; and which, in sodium salt form, has these characteristics:

(c) an approximte elemental composition of 51.87% carbon, 6.05% hydrogen, 13.66% nitrogen, 25.86% oxygen and 2.56% sodium;

(d) an infrared absorption spectrum in KBr pellet as shown in FIG. 3 of the drawings;

(e) contains the following amino acids: aspartic acid, glycine, alanine, serine, threonine, tryptophan, ornithine, kynurenine, and 3-methylglutamic acid;

(f) is soluble in methanol, ethanol, propanol, butanol, dimethylformamide, dimethyl sulfoxide, dioxane, tetrahydrofuran, and water and in acidic and alkaline solutions, except at pH levels of below about pH 3.5; but is only slightly soluble or is insoluble in acetone, chloroform, diethyl ether, benzene, ethyl acetate, and hydrocarbon solvents;

(g) an $R_f$ value of approximately 0.56 on reversed-phase silica-gel TLC in water:methanol:acetonitrile (45:15:40) which contains 0.2% pyridine and 0.2% acetic acid;

(h) the following specific rotation: $[\alpha]_D^{25}+18.6°$ (c 0.9, $H_2O$);

(i) an ultraviolet absorption spectrum in neutral ethanol with the following absorption maxima: 223 ($E^{1\%}_{1\,cm}$303), 260 ($E^{1\%}_{1\,cm}$62), 280 ($E^{1\%}_{1\,cm}$41), 290 ($E^{1\%}_{1\,cm}$36), and 360 nm ($E^{1\%}_{1\,cm}$33); and (j) two titratable groups in 66% aqueous dimethylformamide with $pK_a$ values of approximately 5.9 and 7.6;

or a cationic or acid addition salt of A-21978C factor $C_2$.

8. A compound of claim 7 which is a pharmaceutically acceptable salt of A-21978C factor $C_2$.

9. The compound of claim 7 which is A-21978C factor $C_2$ sodium salt.

10. Antibiotic A-21978C factor $C_3$, which has the following structural formula:

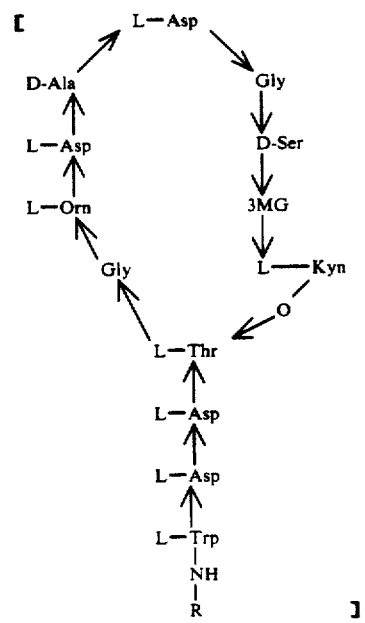

-continued

Figure 4:
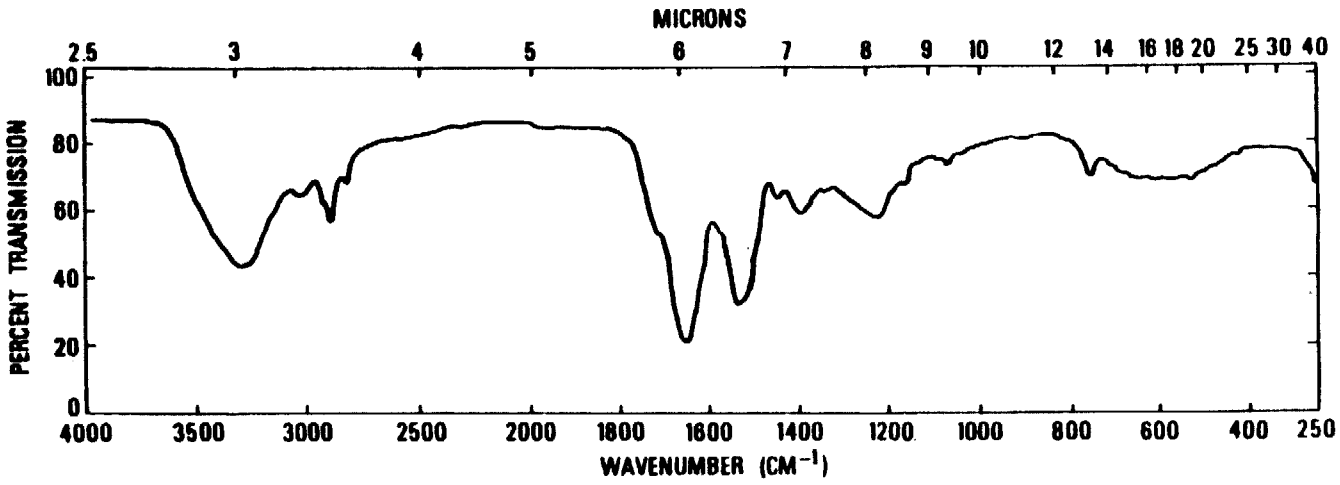

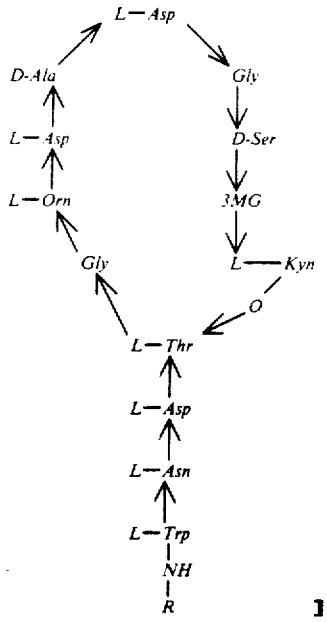

wherein 3MG represents L-threo-3-methylglutamic acid, and R is 10-methyldodecanoyl; and which has:

(a) a molecular formula of approximately [$C_{75}H_{106}N_{16}O_{27}$] $C_{75}H_{107}N_{17}O_{26}$;

(b) a molecular weight of approximately [1664] *1663*; and which, in sodium salt form, has these characteristics:

(c) an approximate elemental composition of 54.18% carbon, 6.35% hydrogen, 13.34% nitrogen, 25.06% oxygen and 1.07% sodium;

(d) an infrared absorption spectrum in KBr pellet as shown in FIG. 4 of the drawings;

(e) upon hydrolysis yields the following amino acids: aspartic acid, glycine, alanine, serine, threonine, tryptophan, ornithine, kynurenine, and 3-methylglutamic acid;

(f) is soluble in methanol, ethanol, propanol, butanol, dimethylformamide, dimethyl sulfoxide, dioxane, tetrahydrofuran, and water and in acidic and alkaline solutions, except at pH levels of below about pH 3.5; but is only slightly soluble or is insoluble in acetone, chloroform, diethyl ether, benzene, ethyl acetate, and hydrocarbon solvents;

(g) an $R_f$ value of approximately 0.47 on reversed-phase silica-gel TLC in water:methanol:acetonitrile (45:15:40) which contains 0.2% pyridine and 0.2% acetic acid;

(h) the following specific rotation: $[\alpha]_D^{25}+20.9°$ (c 0.4, $H_2O$);

(i) an ultraviolet absorption spectrum in neutral ethanol with the following absorption maxima: 223 ($E^{1\%}_{1\,cm}$300), 260 ($E^{1\%}_{1\,cm}$63), 280 ($E^{1\%}_{1\,cm}$42), 290 ($E^{1\%}_{1\,cm}$38), and 360 nm ($E^{1\%}_{1\,cm}$32);

(j) two titratable groups in 66% aqueous dimethylformamide with $pK_a$ values of approximately 5.74 and 7.56;

or a cationic or acid addition salt of A-21978C factor $C_3$.

11. A compound of claim 10 which is a pharmaceutically acceptable salt of A-21978C factor $C_3$.

12. The compound of claim 10 which is A-21978C factor $C_3$ sodium salt.

13. Antibiotic A-21978C factor $C_4$, which has the following structural formula:

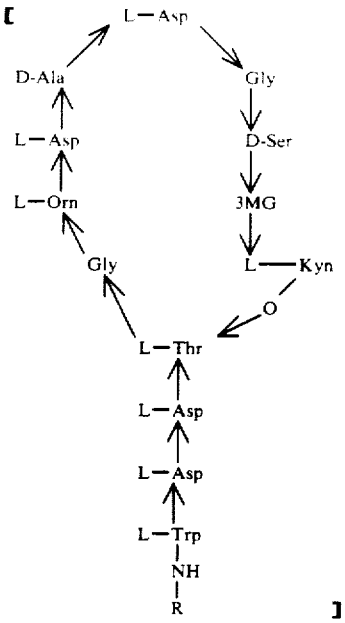

Figure 6:
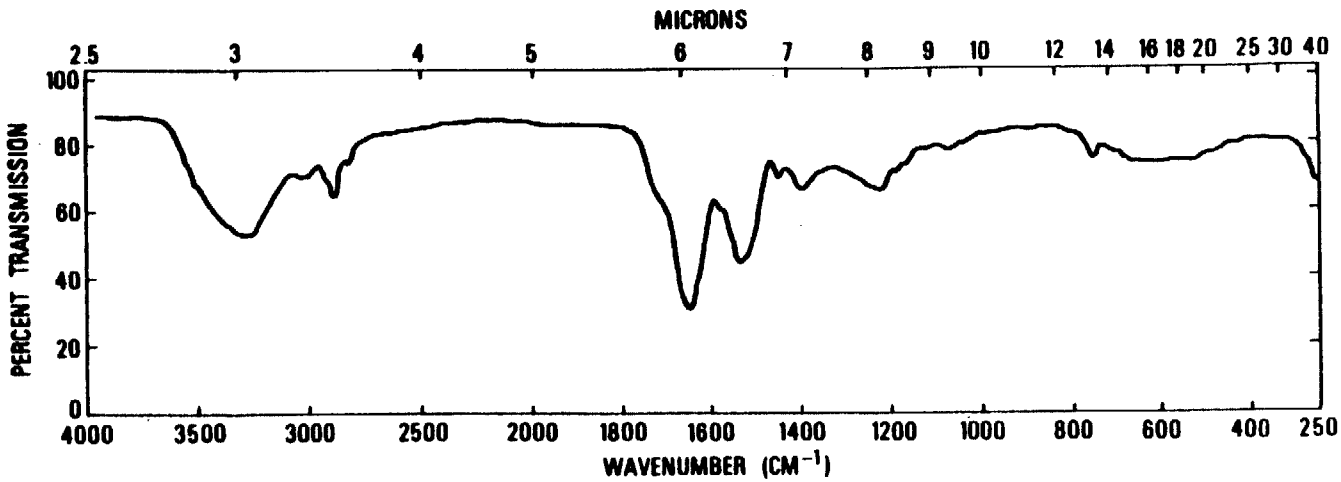

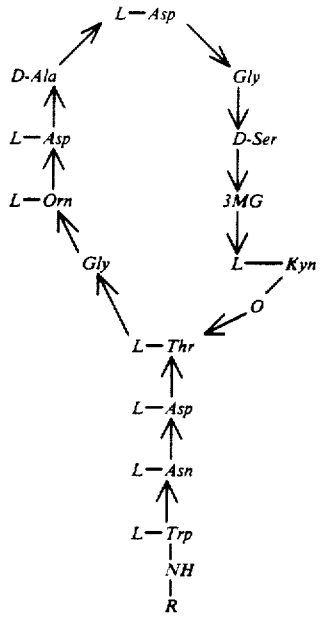

wherein 3MG represents L-threo-3-methylglutamic acid, and R is a $C_{12}$-alkanoyl moiety; and which has:

(a) an approximate molecular formula of [$C_{74}H_{104}N_{16}O_{27}$] $C_{74}H_{105}N_{17}O_{26}$;

(b) an approximate molecular weight of [1650] *1649*; and which, in sodium salt form, has these characteristics:

(c) an approximtae elemental composition of 52.73% carbon, 5.99% hydrogen, 14.07% nitrogen, 25.81% oxygen and 3.4% sodium;

(d) an infrared absorption spectrum in KBr pellet as shown in FIG. 6 of the drawings;

(e) upon hydrolysis yields the following amino acids: aspartic acid, glycine, alanine, serine, threonine, tryptophan, ornithine, kynurenine, and 3-methylglutamic acid;

(f) is soluble in methanol, ethanol, propanol, butanol, dimethylformamide, dimethyl sulfoxide, dioxane, tetrahydrofuran, and water and in acidic and alkaline solutions, except at pH levels of below about pH 3.5; but is only slightly soluble or is insoluble in acetone, chloroform, diethyl ether, benzene, ethyl acetate, and hydrocarbon solvents;

(g) an $R_f$ value of approximately 0.63 on reversed-phase silica-gel TLC in water:methanol:acetonitrile (45:15:40) which contains 0.2% pyridine and 0.2% acetic acid;

(h) the following specific rotation: $[\alpha]_D^{25}+14.8°$ (c 0.7, $H_2O$);

or a cationic or acid addition salt of A-21978C factor $C_4$.

14. A compound of claim 13 which is a pharmaceutically acceptable salt of A-21978C factor $C_4$.

15. The compound of claim 13 which is A-21978C factor $C_4$ sodium salt.

16. Antibiotic A-21978C factor $C_5$, which has the following structural formula:

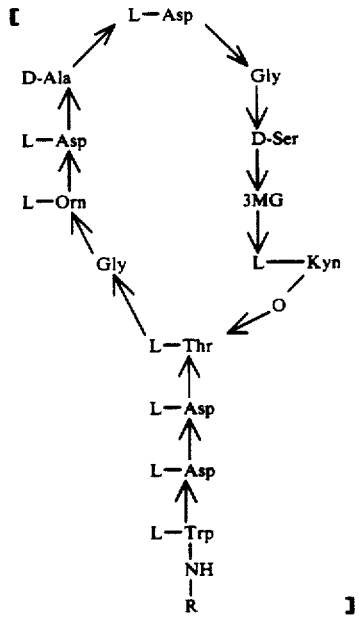

-continued

Figure 7:
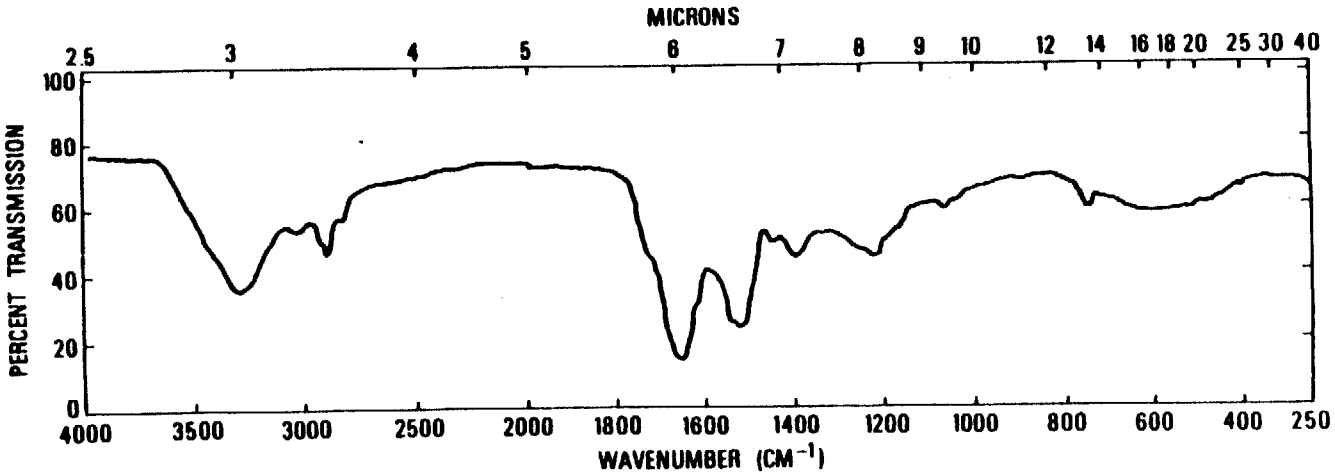

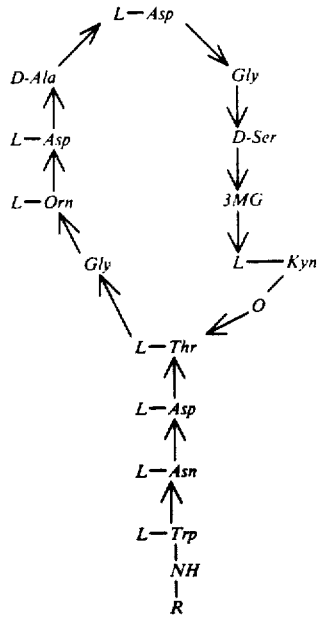

wherein 3MG represents L-threo-3-methylglutamic acid, and R is a $C_{12}$-alkanoyl moiety; and which has:

(a) an approximate molecular formula of [$C_{74}H_{104}N_{16}O_{27}$] $C_{74}H_{105}N_{17}O_{26}$;

(b) an approximate molecular weight of 1650] *1649*; and which, in sodium salt form, has these characteristics:

(c) an approximate elemental composition of 52.76% carbon, 6.71% hydrogen, 13.97% nitrogen, 25.60% oxygen and 1% sodium;

(d) an infrared absorption spectrum as shown in FIG. 7 of the drawings:

(e) upon hydrolysis yields the following amino acids: aspartic acid, glycine, alanine, serine, threonine, tryptophan, ornithine, kynurenine, and 3-methylglutamic acid;

(f) is soluble in methanol, ethanol, propanol, butanol, dimethylformamide, dimethyl sulfoxide, dioxane, tetrahydrofuran, and water and in acidic and alkaline solutions, except at pH levels of below about pH 3.5; but is only slightly soluble or is insoluble in acetone, chloroform, diethyl ether, benzene, ethyl acetate, and hydrocarbon solvents;

(g) an $R_f$ value of approximately 0.53 on reversed-phase silica-gel TLC in water:methanol:acetonitrile (45:15:40) which contains 0.2% pyridine and 0.2% acetic acid:

(h) the following specific rotation: $[\alpha]_D^{25}+17.9°$ (c 0.7, $H_2O$);

or a cationic or acid addition salt of A-21978C factor $C_5$.

17. A compound of claim 16 which is a pharmaceutically acceptable salt of A-21978C factor $C_5$.

18. The compound of claim 16 which is A-21978C factor $C_5$ sodium salt.

* * * * *

UNITED STATES PATENT AND TRADEMARK OFFICE

CERTIFICATE OF CORRECTION

PATENT NO. : RE 32,455 Page 1 of 2

DATED : July 7, 1987

INVENTOR(S) : Robert L. Hamill and Marvin H. Hoehn

It is certified that error appears in the above-identified patent and that said Letters Patent is hereby corrected as shown below:

In Column 4, lines 1 thru 24, and Column 26, lines 26 and 48:

"

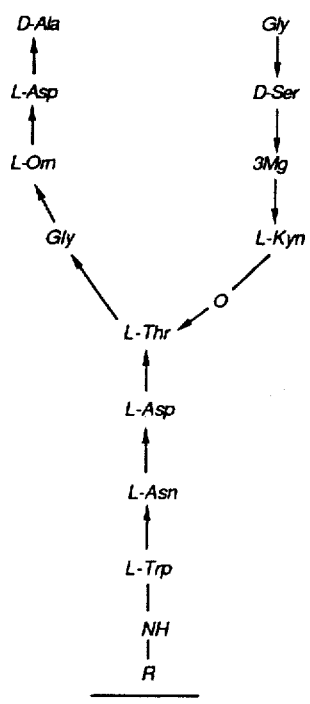

"

should read –

"

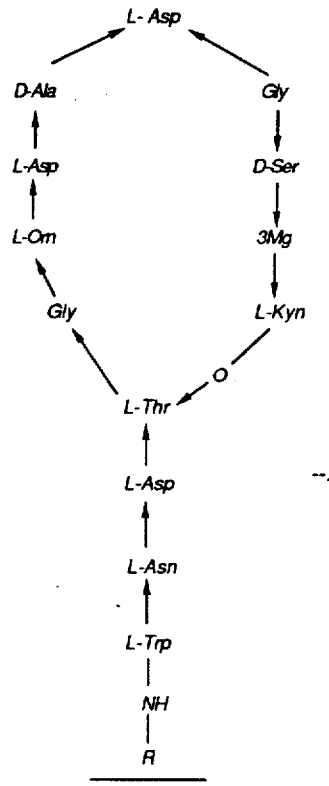

--.

UNITED STATES PATENT AND TRADEMARK OFFICE

CERTIFICATE OF CORRECTION

PATENT NO. : RE 32,455

DATED : July 7, 1987

INVENTOR(S) : Robert L. Hamill and Marvin H. Hoehn

It is certified that error appears in the above-identified patent and that said Letters Patent is hereby corrected as shown below:

In Column 5, line 46:

"$C_1$ [1636] 1635 [$73H_{102}N_{16}O_{27}$] $C_{73}H_{103}N_{17}O_{26}$"

should read

– $C_1$ [1636] 1635 [$C_{73}H_{102}N_{16}O_{27}$] $C_{73}H_{103}N_{17}O_{26}$ –.

In Column 34, line 31: "weight of 1650] " should read -- weight of [1650] –.

Signed and Sealed this

Twenty-sixth Day of March, 1991

*Attest:*

HARRY F. MANBECK, JR.

*Attesting Officer*

*Commissioner of Patents and Trademarks*